US011547696B2

(12) United States Patent
Starczynowski et al.

(10) Patent No.: US 11,547,696 B2
(45) Date of Patent: Jan. 10, 2023

(54) METHODS AND COMPOSITIONS FOR TREATMENT OF MYELODYSPLASTIC SYNDROMES AND/OR ACUTE MYELOID LEUKEMIAS

(71) Applicant: Children's Hospital Medical Center, Cincinnati, OH (US)

(72) Inventors: Daniel Starczynowski, Cincinnati, OH (US); William Seibel, Liberty Township, OH (US); Laura Barreyro, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 320 days.

(21) Appl. No.: 16/332,403

(22) PCT Filed: Oct. 26, 2017

(86) PCT No.: PCT/US2017/058435
§ 371 (c)(1),
(2) Date: Mar. 12, 2019

(87) PCT Pub. No.: WO2018/081361
PCT Pub. Date: May 3, 2018

(65) Prior Publication Data
US 2021/0299102 A1     Sep. 30, 2021

Related U.S. Application Data

(60) Provisional application No. 62/429,958, filed on Dec. 5, 2016, provisional application No. 62/414,021, filed on Oct. 28, 2016.

(51) Int. Cl.
*A61K 31/4184* (2006.01)
*A61K 31/454* (2006.01)
*A61K 45/06* (2006.01)

(52) U.S. Cl.
CPC ........ *A61K 31/4184* (2013.01); *A61K 31/454* (2013.01); *A61K 45/06* (2013.01)

(58) Field of Classification Search
CPC .. A61K 31/4184; A61K 31/454; A61K 45/06; A61P 35/00
See application file for complete search history.

(56) References Cited

U.S. PATENT DOCUMENTS

| | | | |
|---|---|---|---|
| 6,900,235 B1 | 5/2005 | Agyin et al. | |
| 7,608,723 B2 | 10/2009 | Boyce et al. | |
| 8,288,377 B2 | 10/2012 | Storck et al. | |
| 8,501,957 B2 | 8/2013 | Chang et al. | |
| 9,168,257 B2 | 10/2015 | Starczynowski et al. | |
| 9,382,239 B2 | 7/2016 | Gray et al. | |
| 9,458,123 B2 * | 10/2016 | Zhao | A61K 45/06 |
| 9,504,706 B2 | 11/2016 | Starczynowski et al. | |
| 9,855,272 B2 | 1/2018 | Starczynowski et al. | |
| 10,913,736 B2 * | 2/2021 | Buckner | C07D 235/14 |
| 2007/0087392 A1 | 4/2007 | Somers et al. | |
| 2013/0209578 A1 * | 8/2013 | Borden | A61K 31/706 |
| | | | 424/649 |
| 2018/0282734 A1 | 10/2018 | Wells et al. | |

FOREIGN PATENT DOCUMENTS

| | | |
|---|---|---|
| EP | 2 063 962 | 6/2009 |
| WO | WO 03/030902 A1 | 4/2003 |
| WO | WO 2008/030579 A2 | 3/2008 |
| WO | WO 2013/006443 A2 | 1/2013 |
| WO | WO 2013/042137 A1 | 3/2013 |
| WO | WO 2017/075054 A1 | 5/2017 |

OTHER PUBLICATIONS

Adams, A.K., et al., "DEK promotes HPV-positive and -negative head and neck cancer cell proliferation," Oncogene, 2015, 34:868-877, 10 pgs.
Adams, A.K., et al., "IRAK1 is a novel DEK transcriptional target and is essential for head and neck cancer cell survival," Oncotarget, Oct. 2015, 6:43395-43407, 13 pgs.
Alexiadis, V., et al., "The protein encoded by the proto-oncogene DEK changes the topology of chromatin and reduces the efficiency of DNA replication in a chromatin-specific manner," Genes Dev, 2000, 14(11):1308-1312, 5 pgs.
Ang, K.K., et al., "Human Papillomavirus and Survival of Patients with Oropharyngeal Cancer," N Engl J Med, Jul. 2010, 363(1):24-35, 21 pgs.
Bar, et al., "Gene expression patterns in myelodyplasia underline the role of apoptosis and differentiation in disease initiation and progression", Translational Oncogenomics, 3, pp. 137-149, 2008, 13 pgs.
Barreyro, L., et al., "Overexpression of interleukin 1 receptor accessory protein in stem and progenitor cells and outcome correlation in AML and MDS," Blood, 2012, 120(6):1290-1298, 10 pgs.
Boldin, M.P., et al., "miR-146a is a significant brake on autoimmunity, myeloproliferation and cancer in mice", J. Exp. Med. 208, pp. 1189-1201, 2011, 13 pgs.
Breccia, M., et al., "NF-κB as a potential therapeutic target in myelodysplastic syndromes and acute myeloid leukemia", Expert opinion on therapeutic targets, 14, pp. 1157-1176, 2010, 20 pgs.
Buckley, G.M., et al., "IRAK-4 inhibitors. Part 1: a series of amides," Bioorganic & Medicinal Chemistry Letters, 2008, 18:3211-3214, 4 pgs.
Camos, M., et al., "Gene expression profiling of acute myeloid leukemia with translocation t(8;16)(p11;p13) and MYST3-CREBBP rearrangement reveals a distinctive signature with a specific pattern of HOX gene expression", Cancer Res, 66, pp. 6947-6954, 2006, 9 pgs.

(Continued)

*Primary Examiner* — My-Chau T. Tran
(74) *Attorney, Agent, or Firm* — Frost Brown Todd LLC

(57) ABSTRACT

Disclosed are methods for treating a myelodyspastic syndrome (MDS) and/or an acute myeloid leukemia (AML) in an individual in need thereof. Further disclosed are compositions for use in the disclosed methods, used for treating a myelodyspastic syndrome (MDS) and/or an acute myeloid leukemia (AML) in an individual in need thereof.

9 Claims, 25 Drawing Sheets

Specification includes a Sequence Listing.

(56) References Cited

OTHER PUBLICATIONS

Campillos, M., et al., "Transcriptional activation by AP-2α is modulated by the oncogene DEK," Nucleic Acids Res, 2003, 31(5):1571-1575, 5 pgs.
Cerami, E., et al., "The eBio Cancer Genomics Portal: An Open Platform for Exploring Multidimensional Cancer Genomics Data," Cancer Discovery, May 2012, 2(5):401-404, 5 pgs.
Chaturvedi, A.K., et al., "Human Papillomavirus and Rising Oropharyngeal Cancer Incidence in the United States," J Clin Oncol, Nov. 2011, 29(32):4294-4301, 8 pgs.
Chen, G, et al., "Distinctive gene expression profiles of CD34 cells from patients with myelodysplastic syndrome characterized by specific chromosomal abnormalities", Blood, 104, pp. 4210-4218, 2004, 10 pgs.
Chen, J., et al., "ToppGene Suite for gene list enrichment analysis and candidate gene prioritization", Nucleic Acids Res, 37, pp. W305-311, 2009, 7 pgs.
Compound Summary for CID 5375132, PubChem Open Chemistry Database, deposited on Mar. 27, 2005, p. 4, 14 pgs.
Conze, D.B., et al., "Lys63-linked polyubiquitination of IRAK-1 is required for interleukin-1 receptor- and toll-like receptor mediated NF-κB activation", Mol Cell Biol, 28, pp. 3538-3547, 2008, 10 pgs.
Corey, S.J., et al., "Myelodysplastic syndromes: the complexity of stem-cell diseases", Nat Rev Cancer, 7, pp. 118-129, 2007, 13 pgs.
Datta, A., et al., "Oncoprotein DEK as a tissue and urinary biomarker for bladder cancer," BMC Cancer, 2011, 11:234, 7 pgs.
Ebert, B.L., "The biology and treatment of myelodysplastic syndrome", Hematology/oncology clinics of North America, 24, pp. xiii-xvi, 2010, 4 pgs.
Edgar, R., et al., "Gene Expression Omnibus: NCBI gene expression and hybridization array data repository," Nucleic Acids Res, 2002, 30(1):207-210, 4 pgs.
Fang, J., et al., "Cytotoxic effects of bortezomib in myelodysplastic syndrome/acute myeloid leukemia depend on autophagy-mediated lysosomal degradation of TRAF6 and repression of PSMA1," Blood, 2012, 120(4):858-867, 10 pgs.
Flannery, S., et al., "The interleukin-1 receptor-associated kinases: critical regulators of innate immune signaling", Biochem Pharmacol, 80, pp. 1981-1991, 2011, 11 pgs.
Flicek, P., et al., "Ensembl 2012," Nucleic Acids Res, 2012, 40(Database issue):D84-90, 7 pgs.
Gao J, et al., "Integrative Analysis of Complex Cancer Genomics and Clinical Profiles Using the cBioPortal," Science Signaling, Apr. 2013, 6(269):1-19, 19 pgs.
Gennaro, A.R., (ed.), *Remington's Pharmaceutical Sciences*, 18th Ed., 1990, Mack Publishing Company, Easton, Pennsylvania, Table of Contents only, 8 pgs.
Gennaro, A.R., (ed.), *Remington: The Science and Practice of Pharmacy*, 20th Ed., 2000, Lippincott Williams & Wilkins, Table of Contents Only, 5 pgs.
Gondek, L.P., et al., "Chromosomal lesions and uniparental disomy detected by SMP arrays in MDS, MDS/MPD, and MDS-derived AML", Blood, 111, pp. 1534-1542, 2008, 9 pgs.
Greenberg, P., et al., "International scoring system for evaluating prognosis in myelodysplastic syndromes", Blood, 89, pp. 2079-2088, 1997, 11 pgs.
Greenberg, P.L., "Current therapeutic approaches for patients with myelodysplastic syndromes", Br J Haematol, 150, pp. 131-143, 2010, 13 pgs.
Hofmann, W.K., et al., "Characterization of gene expression of CD34+ cells from normal and myelodysplastic bone marrow", Blood, 100, pp. 3553-3560, 2002, 8 pgs.
Hung, P-S., et al., "miR-146a Enhances the Oncogenicity of Oral Carcinoma by Concomitant Targeting of the IRAK1, TRAF6 and NUMB Genes," PloS One, 2013, 8(11):e79926, 17 pgs.
Kavanaugh, G.M., et al., "The human DEK oncogene regulates DNA damage response signaling and repair," Nucleic Acids Res, 2011, 39(17):7465-7476, 12 pgs.

Khodadoust, M.S., et al., "Melanoma Proliferation and Chemoresistance Controlled by the DEK Oncogene," Cancer Res, Aug. 2009, 69(16):6405-6413, 9 pgs.
Ko, S-I., et al., "Regulation of histone acetyltransferase activity of p300 and PCAF by proto-oncogene protein DEK," FEBS Letters, 2006, 580(13):3217-3222, 6 pgs.
Koch, A.T., et al., "MyD88-Dependent Signaling Decreases the Antitumor Efficacy of Epidermal Growth Factor Receptor Inhibition in Head and Neck Cancer Cells," Cancer Res, 2015, 75(8):1657-1667, 11 pgs.
Koleva, R.I., et al., "C/EBPα and DEK coordinately regulate myeloid differentiation," Blood, 2012, 119(21):4878-4888, 39 pgs.
Kollewe, C., et al., "Sequential autophosphorylation steps in the interleukin-1 receptor-associated kinase-1 regulate its availability as an adapter in interleukin-1 signaling", J Biol Chem, 279, pp. 5227-5236, 2004, 10 pgs.
Komurov, K., et al., "NetWalker: a contextual network analysis tool for functional genomics," BMC Genomics, 2012, 13:282, 9 pgs.
Kristinsson, S.Y., et al., "Chronic immune stimulation might act as a trigger for the development of acute myeloid leukemia or myelodysplastic syndromes", J. Clin Oncol, 29, pp. 2897-2903, 2011, 7 pgs.
Martin, M.G., et al., "Limited engraftment of low-risk myelodysplastic syndrome cells in NOD/SCID gamma-C chain knockout mice", Leukemia, 24, pp. 1662-1664, 2011, 3 pgs.
Marur, MD, S., et al., "Head and Neck Cancer: Changing Epidemiology, Diagnosis, and Treatment," Mayo Clinic Proceedings, 2008, 83(4):489-501, 13 pgs.
Matsuoka, A., et al., "Lenalidomide induces cell death in an MDS-derived cell line with deletion of chromosome 5q by inhibition of cytokinesis", Leukemia, 24, pp. 748-755, 2010, 8 pgs.
Mor-Vaknin, N., et al., "DEK in the Synovium of Patients With Juvenile Idiopathic Arthritis: Characterization of DEK Antibodies and Posttranslational Modification of the DEK Autoantigen," Arthritis and Rheumatism, Feb. 2011, 63(2):556-567, 12 pgs.
Mor-Vaknin, N., et al., "The DEK Nuclear Autoantigen Is a Secreted Chemotactic Factor," Mol Cell Biol, 2006, 26(24):9484-9496, 13 pgs.
Ngo, V.N., et al., "Oncogenically active MYD88 mutations in human lymphoma", Nature, 470, pp. 115-119, 2010, 7 pgs.
Nimer, S.D., "Myelodysplastic syndromes", Blood, 111, pp. 4841-4851, 2008, 12 pgs.
O'Dwyer, M.E., et al., "ST1571 as a targeted therapy for CML", Cancer Invest, 21, pp. 429-438, 2003, 12 pgs.
Park, C., et al., "Hematopoietic Stem Cells Are the Disease-Initiating Cells in the Myelodysplastic Syndromes", Paper presented at: ASH Annual Meeting, (San Diego, CA) 2011, Abstract Only, 1 pg.
Pellagatti, A., et al. "Deregulated gene expression pathways in myelodysplastic syndrome hematopoietic stem cells", Leukemia, 24, pp. 756-764, 2010, 9 pgs.
Pellagatti, A., et al. "Gene expression profiles of CD34+ cells in myelodysplastic syndromes: involvement of interferon-stimulated genes and correlation to FAB subtype and karyotype", Blood, 108, pp. 337-345, 2006, 10 pgs.
Powers, J.P., et al., "Discovery and initial SAR inhibitors of interleukin-1 receptor-associated kinase-4", Bioorganic & Medicinal Chemistry Letters, Pergamon, Amsterdam, NL, vol. 16, No. 11, Jun. 1, 2006, pp. 2842-2845, 4 pgs.
Privette Vinnedge, L.M., et al., "The DEK Oncogene Is a Target of Steroid Hormone Receptor Signaling in Breast Cancer," PloS One, 2012, 7(10):e46985, 10 pgs.
Privette Vinnedge, L.M., et al., "The DEK oncogene promotes cellular proliferation through paracrine Wnt signaling in Ron receptor-positive breast cancers," Oncogene, 2015, 34:2325-2336, 12 pgs.
Privette Vinnedge, L.M., et al., "The human DEK oncogene stimulates β-catenin signaling, invasion and mammosphere formation in breast cancer," Oncogene, 2011, 30(24):2741-2752, 12 pgs.
Rhyasen, G.W., et al., "IRAK signalling in cancer," British Journal of Cancer, 2015, 112:232-237, 6 pgs.
Rhyasen, G.W., et al., "Targeting IRAK1 as a Therapeutic Approach for Myelodysplastic Syndrome," Cancer Cell, Jul. 2013, 24(1):90-104, 15 pgs.

(56) References Cited

OTHER PUBLICATIONS

Sammons, M., et al., "Negative Regulation of the RelA/p65 Transactivation Function by the Product of the DEK Proto-oncogene," J Biol Chem, 2006, 281(37):26802-26812, 11 pgs.
Sandén, C., et al., "The DEK oncoprotein binds to highly and ubiquitously expressed genes with a dual role in their transcriptional regulation," Molecular Cancer, 2014, 13:215, 13 pgs.
Sawatsubashi, S., et al., "A histone chaperone, DEK, transcriptionally coactivates a nuclear receptor," Genes Dev, 2010, 24(2):159-170, 13 pgs.
Sekeres, M.A., "Are we nearer to curing patients with MDS?", Best Preact Res Clin Haematol, 23, pp. 481-487, 2010a, 7 pgs.
Sekeres, M.A., "The epidemiology of myelodysplastic syndromes", Hematology/oncology clinics of North America, 24, pp. 287-294, 2010b, 8 pgs.
Shibata, T., et al., "DEK oncoprotein regulates transcriptional modifiers and sustains tumor initiation activity in high-grade neuroendocrine carcinoma of the lung," Oncogene, 2010, 29(33):4671-4681, 11 pgs.
Sokol, L., et al., "Identification of a risk dependent microRNA expression signature in myelodysplastic syndromes", Br J Haematol, 153, pp. 24-32, 2011, 9 pgs.
Srivastava, R., et al., "Augmentation of therapeutic responses in melanoma by inhibition of IRAK-1,-4," Cancer Res, 2012, 72(23):6209-6216, 29 pgs.
Starczynowski, D.T., et al., "Genome-wide identification of human microRNAs located in leukemia-associated genomic alterations", Blood, 117, pp. 595-607, 2011b, 11 pgs.
Starczynowski, D.T., et al., "Identification of miR-145 and miR-146a as mediators of the 5q-syndrome phenotype," Nat Med, Jan. 2010, 16(1):49-58, 11 pgs.
Starczynowski, D.T., et al., "Innate immune signaling in the myelodysplastic syndromes", Henatol Oncol Clin North Am, 24, pp. 343-359, 2010, 17 pgs.
Starczynowski, D.T., et al., "MicroRNA-146a disrupts hematopoietic differentiation and survival", Exp Hematol, 39, pp. 167-178, e164, 2011a, 16 pgs.
Starczynowski, D.T., et al., "TRAF6 is an amplified oncogene bridging the RAS and NF-κB pathways in human lung cancer", J Clin Invest, 121, pp. 4095-4105, 2011, 11 pgs.
Subramanian, A., et al. "Gene set enrichment analysis: a knowledge-bases approach for interpreting genome-wide expression profiles", Proc Natl Acad Sci USA, 102, pp. 15545-15550, 2005, 6 pgs.
Taganov, K.D., et al., "NF-κB-dependent induction of microRNA miR-146, an inhibitor targeted to signaling proteins of innate immune responses", Proc Natl Acad Sci USA, 103, pp. 12481-12486, 2006, 6 pgs.
Tehranchi, R., et al., "Persistent malignant stem cells in del(5q) myelodysplasia in remission", N Engl J Med, 363, pp. 1025-1037, 2010, 13 pgs.
Thomadaki, H., et al., "Molecular profile of the BCL2 family of the apoptosis related genes in breast cancer cells after treatment with cytotoxic/cytostatic drugs", Connect Tissue Res, 49, pp. 261-264, 2008, 6 pgs.
Tohyama, K., et al., "A novel factor-dependent human myelodysplastic cell line, MDS92, contains haemopoietic cells of several lineages", Br J Haimatol, 91, pp. 795-799, 1995, 5 pgs.
Troy, D.B., (ed.), *Remington: The Science and Practice of Pharmacy*, 21$^{st}$ Ed., 2005, Lippincott Williams & Wilkins Publishing, Philadelphia, Table of Contents only, 6 pgs.

Tse, C., et al., "ABT-263: a potent and orally bioavaiiable Bcl-2 family inhibitor", Cancer Res, 68, pp. 3421-3428, 2008, 9 pgs.
*The United States Pharmacopeia: the National Formulary* (USP 24 NF 19), by authority of the United States Pharmacopeial Convention, Inc., meeting at Washington, D.C., Mar. 9-12, 1995. Prepared by the Committee of Revision and published by the Board of Trustees, Official from Jan. 1, 2000, 1999, Table of Contents only, 4 pgs.
Valk, P.J., et al., Prognostically useful gene-expression profiles in acute myeloid leukemia, N Engl J Med, 350, pp. 1617-1628, 2004, 12 pgs.
Vanderwerf, S.M., et al., "TLR8-dependent TNF-α overexpression in Fanconi anemia group C cells," Blood, 114, pp. 5290-5298, 2009, 10 pgs.
Vasikova, A., et al., "A distinct expression of various gene subsets in CD34+ cells from patients with early and advanced myelodysplastic syndrome", Leuk Res, 34, pp. 1566-1572, 2010, 7 pgs.
Wang, Z., et al., "IRAK-4 Inhibitors for Inflammation", Current Topics in Medicinal Chemistry, May 1, 2009, pp. 727-734, 14 pgs.
Wei, Y., et al., "Deregulation of TLR2-JMJD3 Innate Immunity Signaling, Including a Rare TLR2 SNP As a Potential Somatic Mutation, in Myelodysplastic Syndromes (MDS)", In American Society of Hematology, (Atlanta, GA) 2012, Abstract Only, 1 pg.
Wise-Draper, T.M., et al., "Apoptosis Inhibition by the Human DEK Oncoprotein Involves Interference with p53 Functions," Mol Cell Biol, Oct. 2006, 26(20):7506-7519, 14 pgs.
Wunderlich, M, et al, "AML xenograft efficiency is significantly improved in NOD/SCID-IL2RG mice constitutively expressing human SCF, GM-CSF and IL-3," Leukemia, 2010, 24:1785-1788, 5 pgs.
Xie, X., et al., "Systematic discovery of regulatory motifs in human promoters and 3' UTRs by comparison of several mammals," Nature, Mar. 2005, 434(7031):338-345, 19 pgs.
Yang, Y.F., et al., "Interleukin-1 receptor associated kinases-1/4 inhibition protects against acute hypoxia/ischemia-induced neuronal injury in vivo and in vitro", Neuroscience, 196, pp. 25-34, 2011, 10 pgs.
Zhao, J.L., et al., "NF-κB dysregulation in micro-RNA-146a-deficint mice drives the development of myeloid malignancies", Proc Natl Acad Sci USA, 108, pp. 9184-9189, 2011, 6 pgs.
International Search Report and Written Opinion dated Nov. 20, 2014 for Application No. PCT/US2014/039156, 12 pgs.
International Search Report and Written Opinion dated Jan. 3, 2018 for Application No. PCT/US2017/058435, 10 pgs.
International Search Report and Written Opinion dated Jan. 19, 2017 for Application No. PCT/US2016/058864, 11 pgs.
U.S. Appl. No. 61/826,211, filed May 22, 2013, by Starczynowski et al., Entitled: "Combination Therapy for MDS".
U.S. Appl. No. 62/248,050, filed Oct. 29, 2015, by Wells et al., Entitled: "Methods and Compositions for the Treatment of Head and Neck Cancer".
U.S. Appl. No. 62/414,021, filed Oct. 28, 2016, by Starczynowski et al., Entitled: "Inhibition of UBE2N as a Therapeutic Approach in Myelodysplastic Syndrome (MDS) and Acute Myeloid Leukemia (AML)".
U.S. Appl. No. 62/429,958, filed Dec. 5, 2016, by Starczynowski et al., Entitled: "Inhibition of UBE2N as a Therapeutic Approach in Myelodysplastic Syndromes and Acute Myeloid Leukemia".

* cited by examiner

METHODS AND COMPOSITIONS FOR TREATMENT OF MYELODYSPLASTIC SYNDROMES AND/OR ACUTE MYELOID LEUKEMIAS

CROSS REFERENCE TO RELATED APPLICATIONS

This application claims priority to and the benefit of International Application No. PCT/US2017/058435, filed Oct. 26, 2017 entitled "Methods and Compositions for Treatment of Myelodysplastic Syndromes and/or Acute Myeloid Leukemias," which claims priority to and the benefit of U.S. Provisional Patent Application Ser. No. 62/429,958, filed Dec. 5, 2016, to Starczynowski, entitled "Inhibition of UBE2N as a Therapeutic Approach in Myelodysplastic Syndromes and Acute Myeloid Leukemia," and U.S. Provisional Patent Application Ser. No. 62/414,021, filed Oct. 28, 2016, to Starczynowski, entitled "Inhibition of UBE2N as a Therapeutic Approach in Myelodysplastic Syndromes (MDS) and Acute Myeloid Leukemia (AML)," the contents of all are incorporated by reference in their entirety.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 16332403 SequenceListing_ST25.txt, the date of the creation of the ASCII text file is Oct. 21, 2020, and the size of the ASCII text file is 881 bytes.

BACKGROUND

Myelodysplastic Syndromes (MDS) are malignant, potentially fatal blood diseases that arise from a defective hematopoietic stem/progenitor cell. MDS are heterogeneous diseases with few treatment options. One of the key challenges facing MDS treatment is the lack of effective medicines capable of providing a durable response.

MDS are hematologic malignancies defined by blood cytopenias due to ineffective hematopoiesis, and a predisposition to acute myeloid leukemia (AML) (Corey et al., 2007; Nimer, 2008). MDS is most prominent in individuals over 60 years of age, and as a result of longer life expectancies, the incidence of MDS has escalated in recent years (Sekeres, 2010b). MDS is fatal in majority of patients as a result of marrow failure, immune dysfunction, and/or transformation to overt leukemia. Current treatment options for MDS include allogeneic HSC transplantation, demethylating agents, and immunomodulatory therapies (Ebert, 2010). At present, the only curative treatment for MDS is (hemopoeitic stem cell) HSC transplantation, an option unavailable to many of the older patients. Instead, these patients receive supportive care and transfusions to ameliorate their disease complications. Unfortunately, even with this treatment, the MDS clones persist in the marrow and the disease invariably advances (Tehranchi et al., 2010). For advanced disease or high-risk MDS, patients may also receive immunosuppressive therapy, epigenetic modifying drugs, and/or chemotherapy (Greenberg, 2010). Despite recent progress, most MDS patients exhibit treatment-related toxicities or relapse (Sekeres, 2010a). Overall the efficacy of these treatments is variable, and generally life expectancies are only slightly improved as compared to supportive care.

Approximately 30% of MDS patients also develop aggressive Acute Myeloid leukemia (AML) due to acquisition of additional mutations in the defective hematopoietic stem/progenitor cell (HSPC) (Greenberg et al., 1997). AML is a cancer of the myeloid line of blood cells, characterized by the rapid growth of abnormal white blood cells that accumulate in the bone marrow and interfere with the production of normal blood cells. AML is the most common acute leukemia affecting adults, and its incidence increases with age. Although AML is a relatively rare disease, accounting for approximately 1.2% of cancer deaths in the United States, its incidence is expected to increase as the population ages. Several risk factors and chromosomal abnormalities have been identified, but the specific cause is not clear. As an acute leukemia, AML progresses rapidly and is typically fatal within weeks or months if left untreated. The prognosis for AML that arises from MDS has a worse as compared to other types of AML.

Consequently, there is an urgent need to develop targeted therapies capable of eliminating the MDS-initiating clones, and for treatments and method of treating MDS and AML. Identification of molecular targets is essential to improve outcome and eliminate the MDS-causing clones and/or AML. Herein, therapeutic targets and agents for treating MDS and/or AML are described.

BRIEF SUMMARY

Disclosed are methods for treating a myelodyspastic syndrome (MDS) and/or an acute myeloid leukemia (AML) in an individual in need thereof. Further disclosed are compositions for use in the disclosed methods, used for treating a myelodyspastic syndrome (MDS) and/or an acute myeloid leukemia (AML) in an individual in need thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
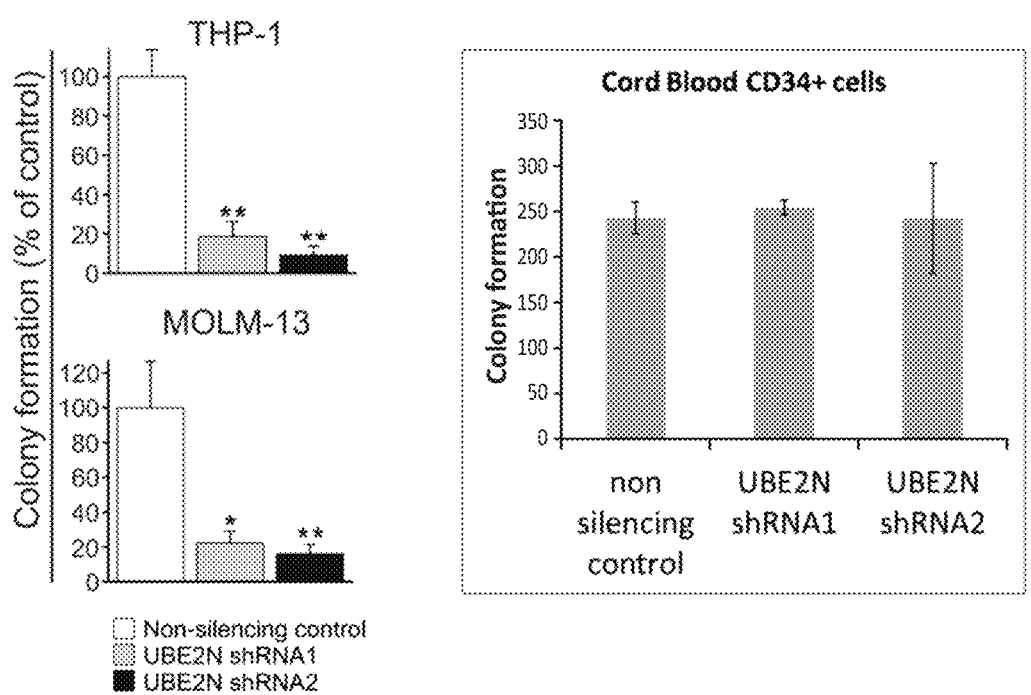
FIG. 1. Knockdown of UBE2N with lentivirally expressed shRNAs abrogates AML cell clonogenic potential.
Figure 2:
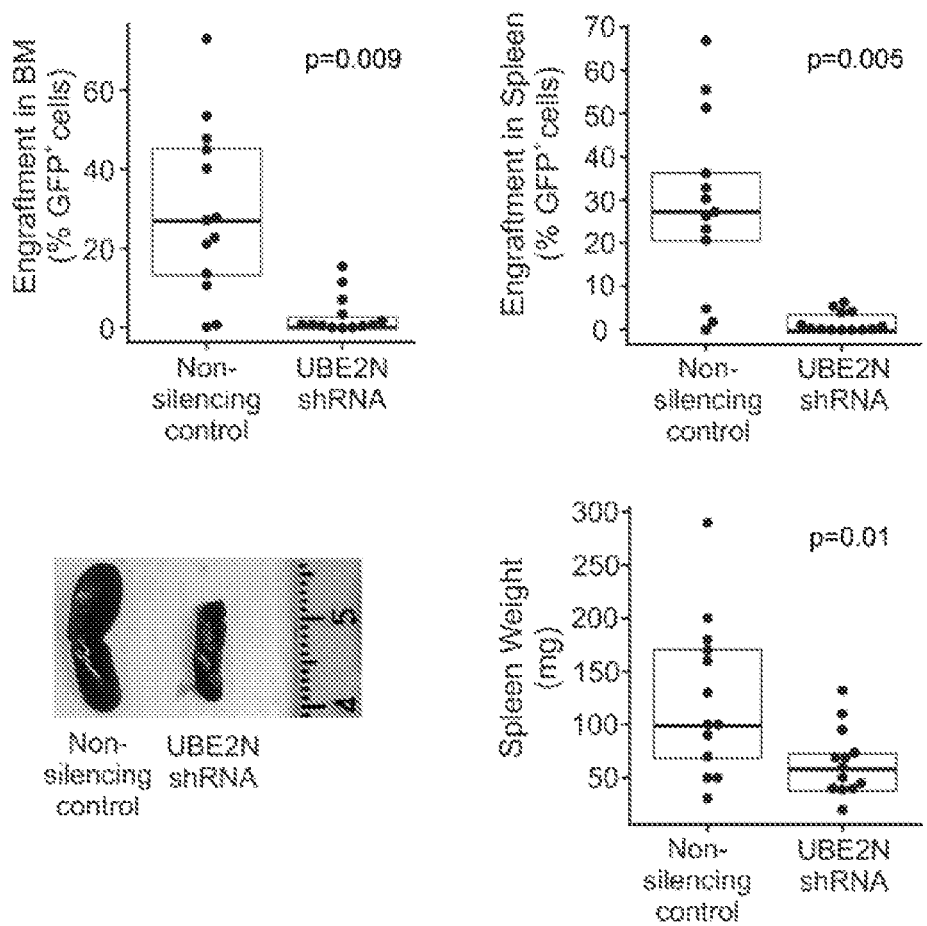
FIG. 2. Knockdown of UBE2N with lentivirally expressed shRNAs abrogates engraftment of AML cells in NSG mice.
Figure 3:
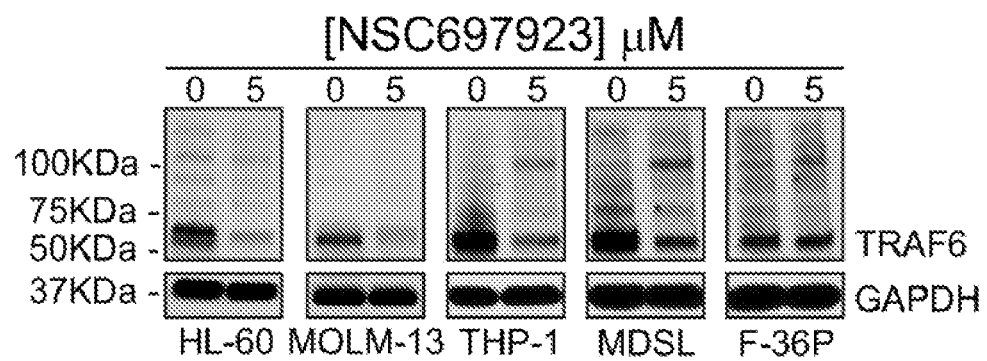
FIG. 3. Pharmacological inhibition of UBE2N with NSC23 inhibits NKkB and interferon signaling in AML/MDS cells FIG. 4. Pharmacological inhibition of UBE2N with NSC23 inhibits NFkB and interferon signaling in AML/MDS cells.
Figure 4:
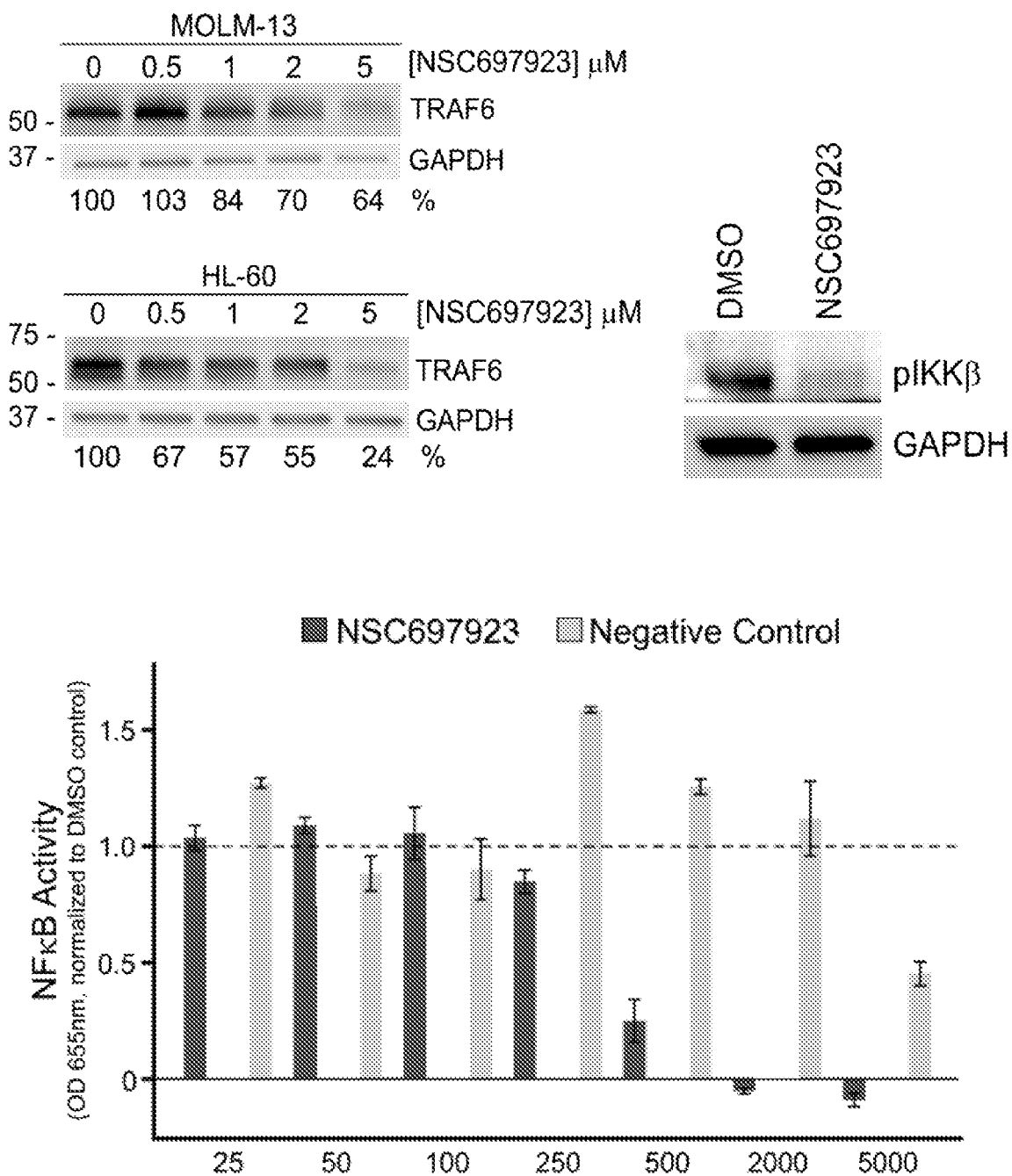
Figure 5:
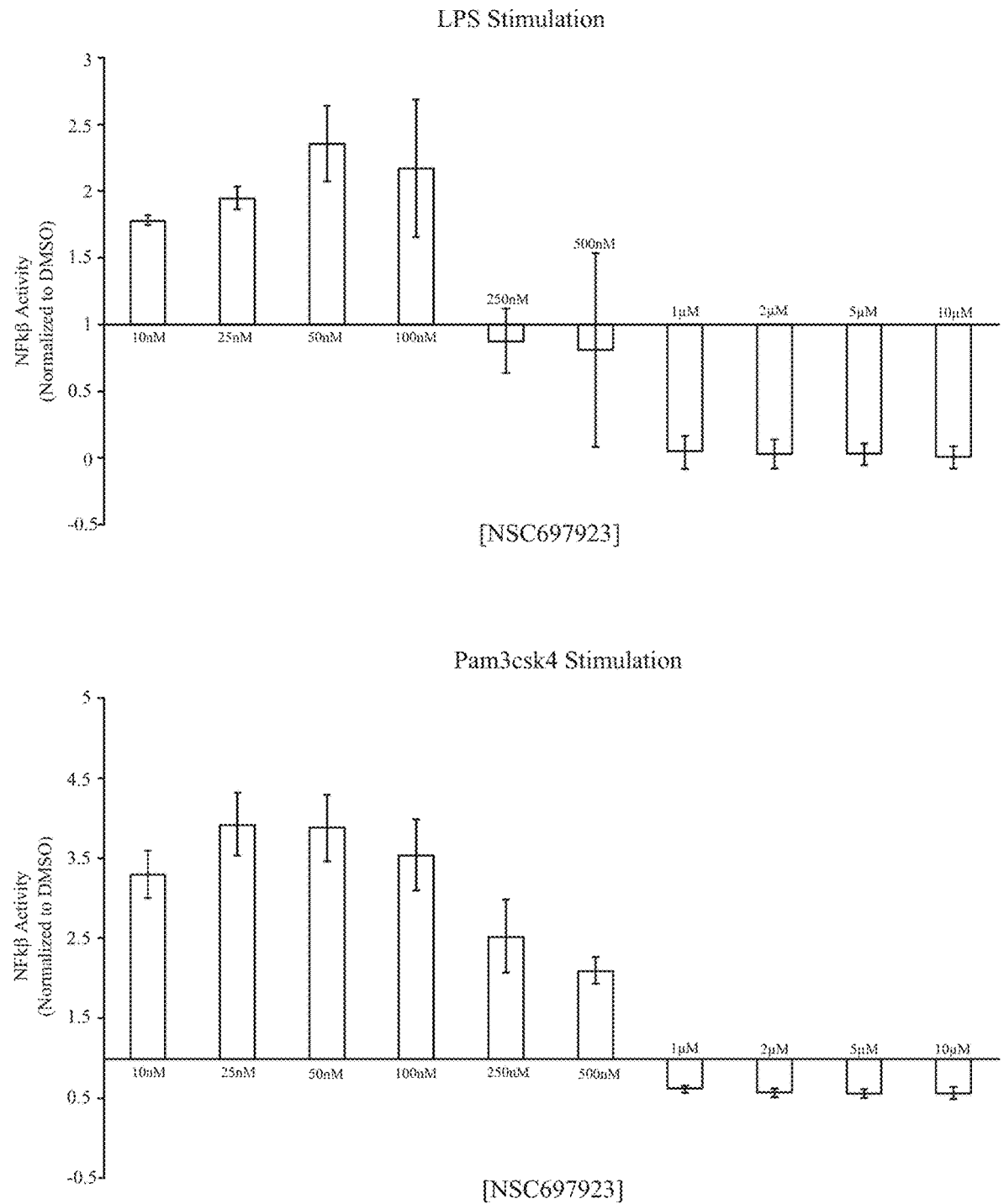
FIG. 5. Pharmacological inhibition of UBE2N with NSC23 inhibits TLR mediated NFkB activity.
Figure 6:
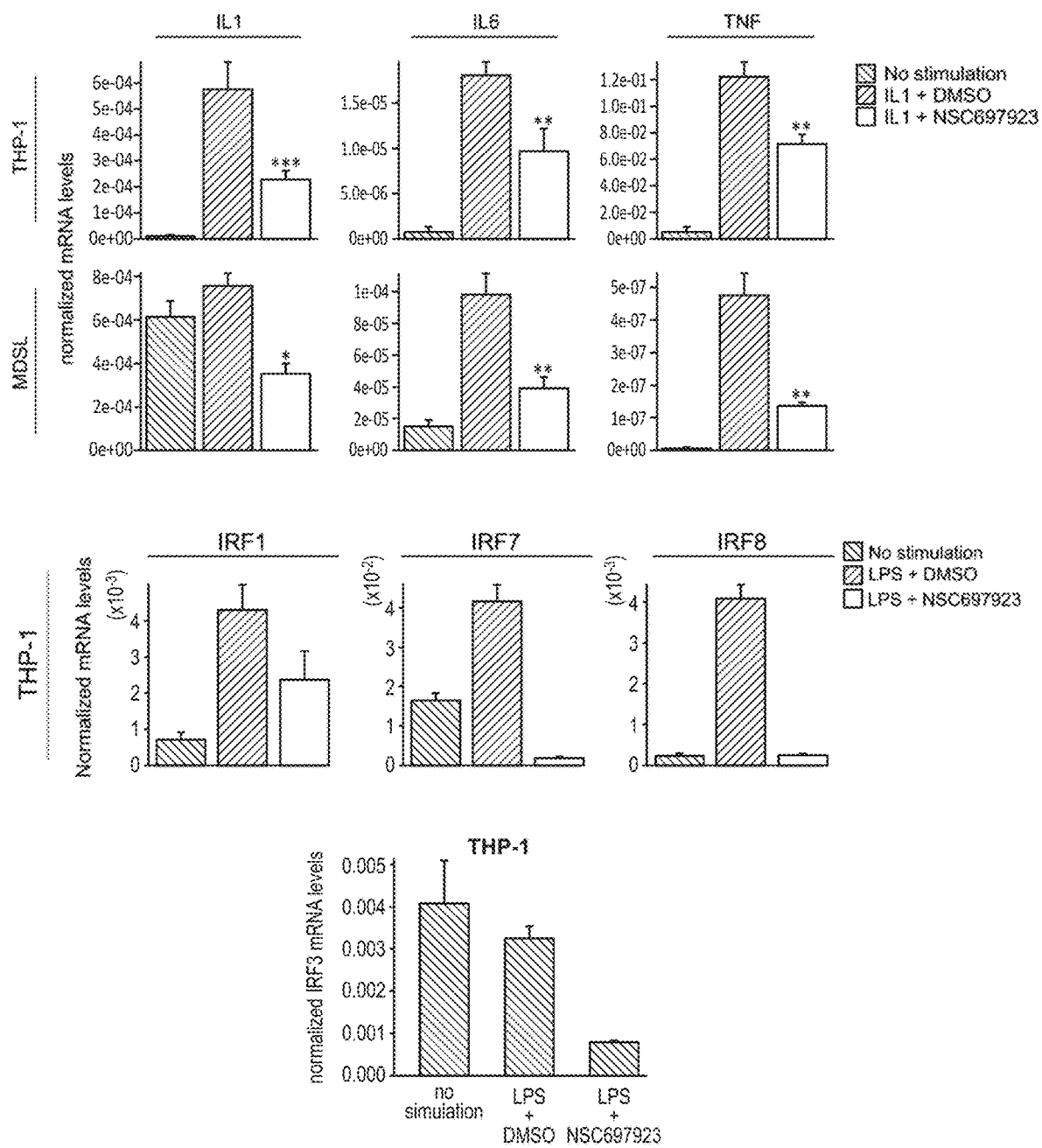
FIG. 6. Pharmacological inhibition of UBE2N with NSC23 inhibits NFkB and interferon signaling in AML/MDS cells.
Figure 7:
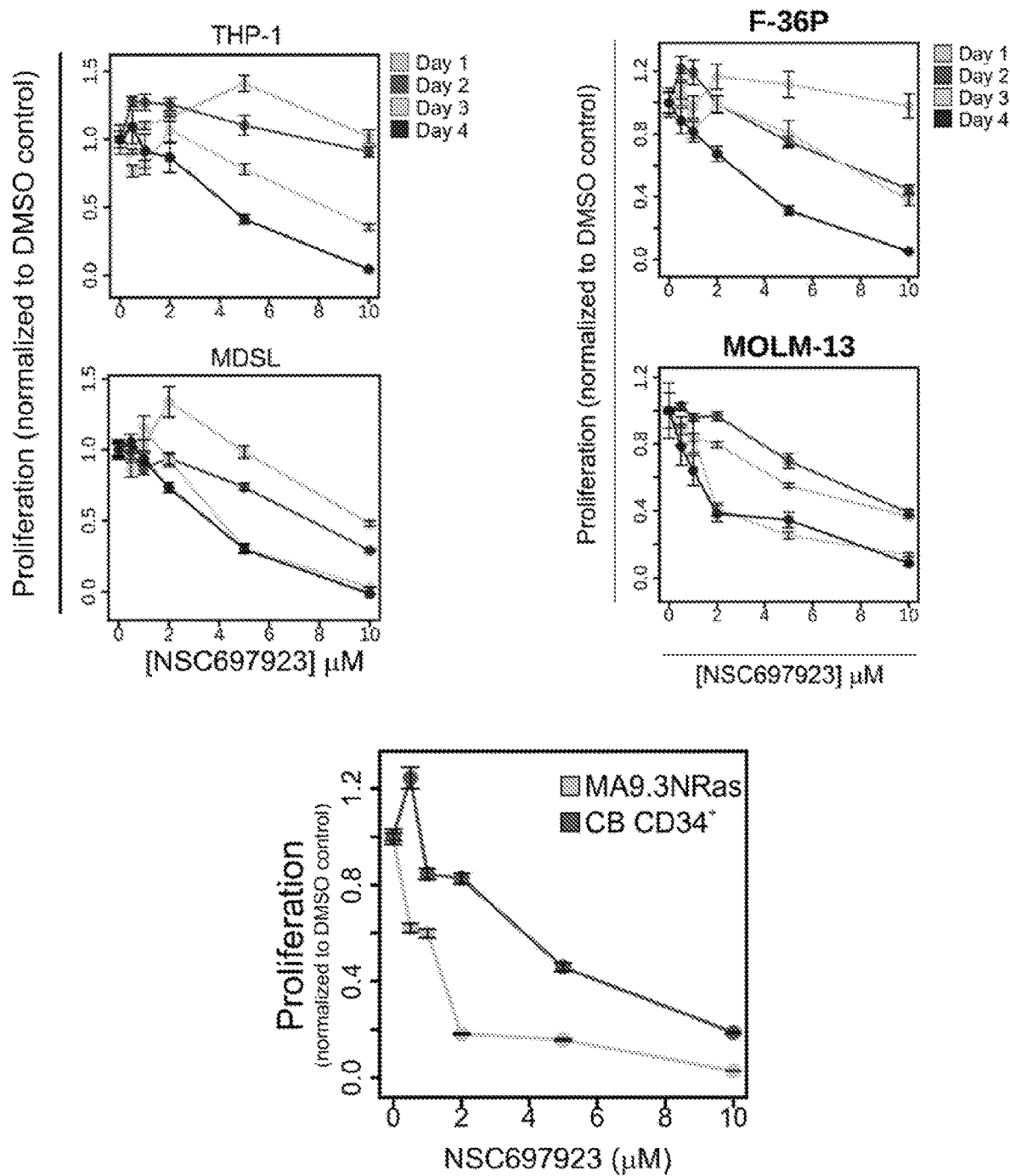
FIG. 7. Pharmacological inhibition of UBE2N with NSC23 reduces proliferation and clonogenic potential of AML/MDS cells.
Figure 8:
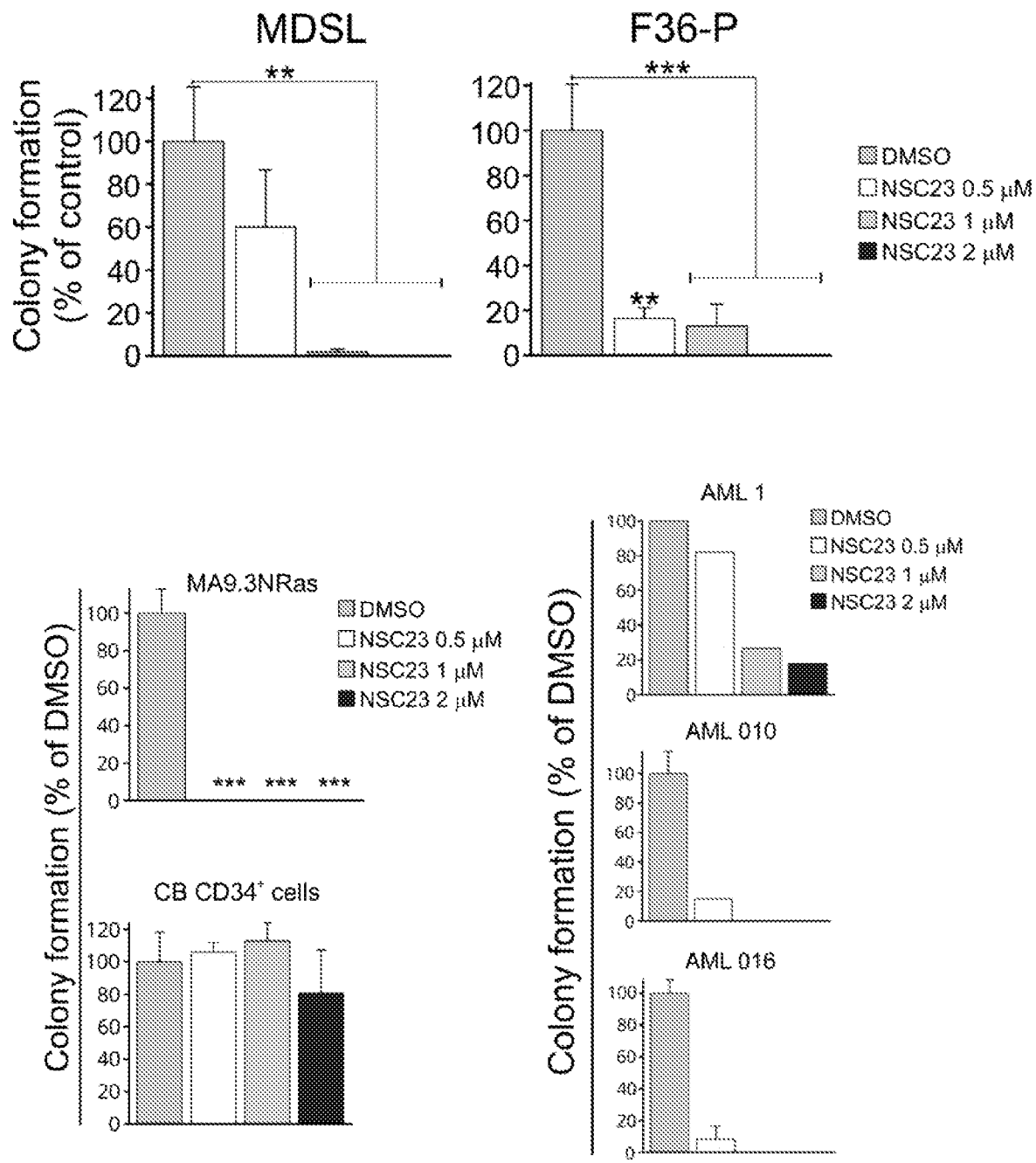
FIG. 8. Pharmacological inhibition of UBE2N with NSC23 reduces proliferation and clonogenic potential of AML/MDS cells.
Figure 9:
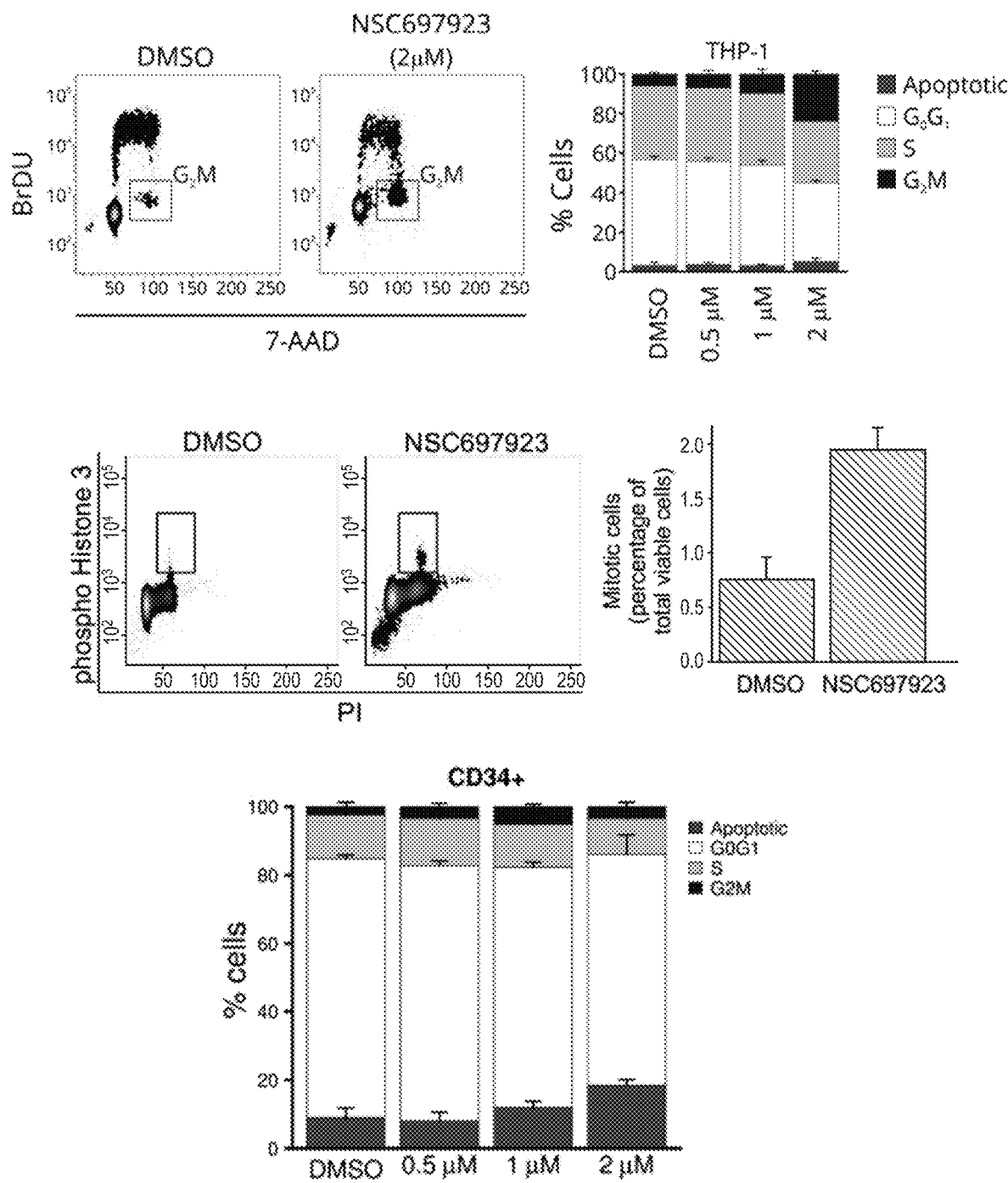
FIG. 9. Pharmacological inhibition of UBE2N with NSC23 induces cell cycle arrest in mitosis and cell death of AML/MDS cells.
Figure 10:
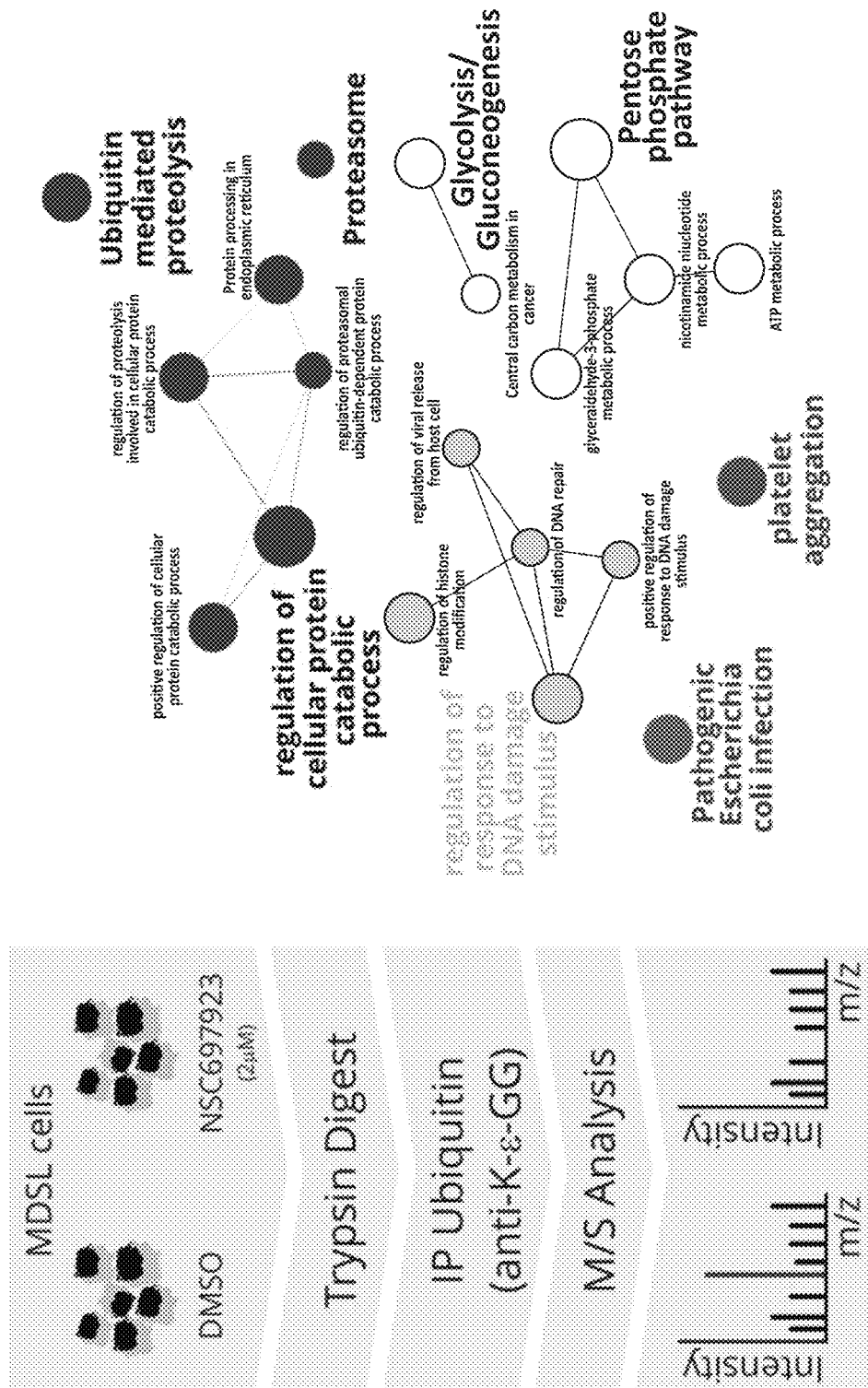
FIG. 10. Differential protein ubiquination in MDSL cells upon NSC23 treatment.
Figure 11:
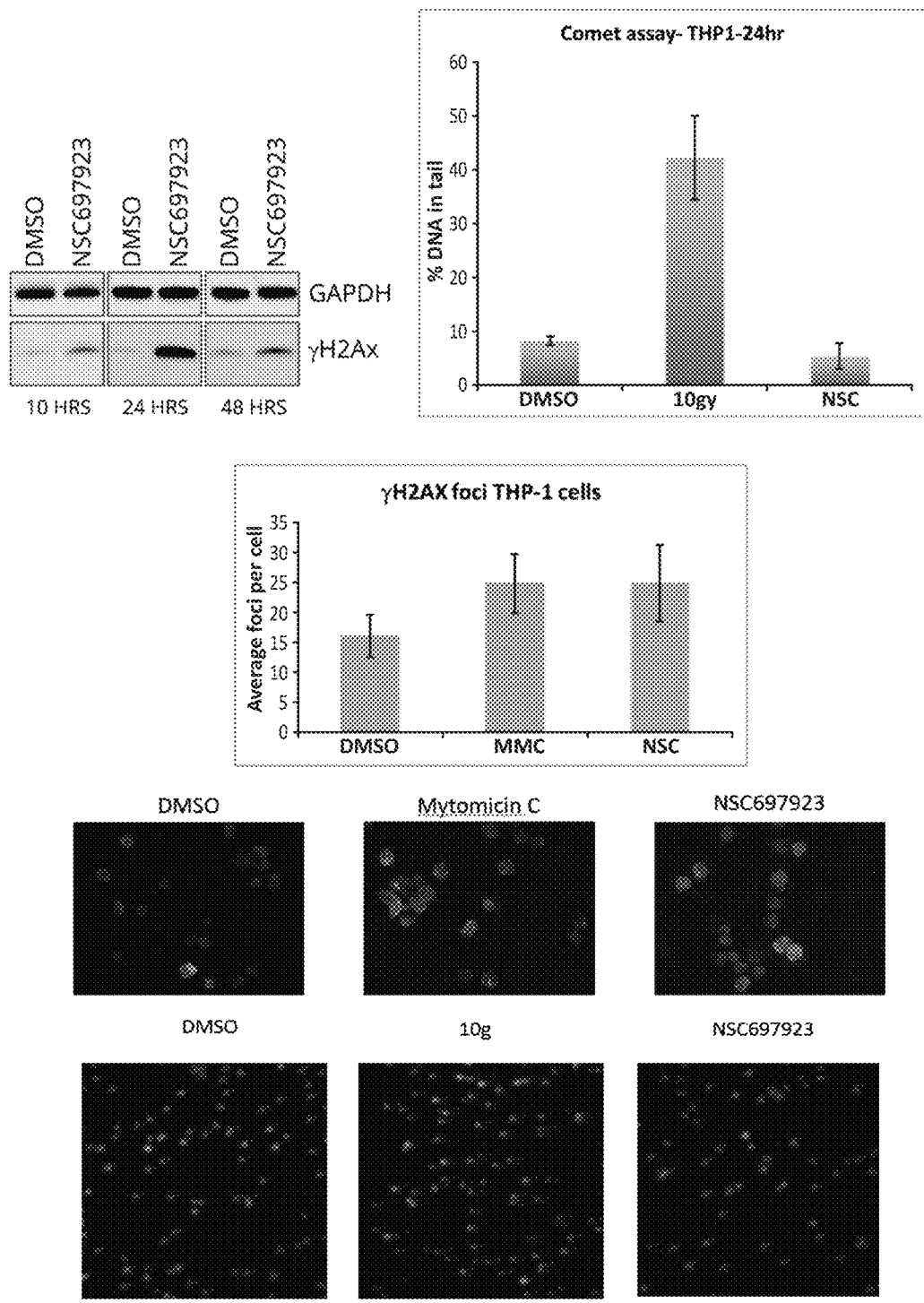
FIG. 11. Pharmacological inhibition of UBE2N with NSC23 induces DNA damage, cell cycle arrest in mitosis and cell death of AML/MDS FIG. 12. Pharmacological inhibition of UBE2N with NSC23 induces DNA damage, cell cycle arrest in mitosis and cell death of AML/MDS cells.
Figure 12:
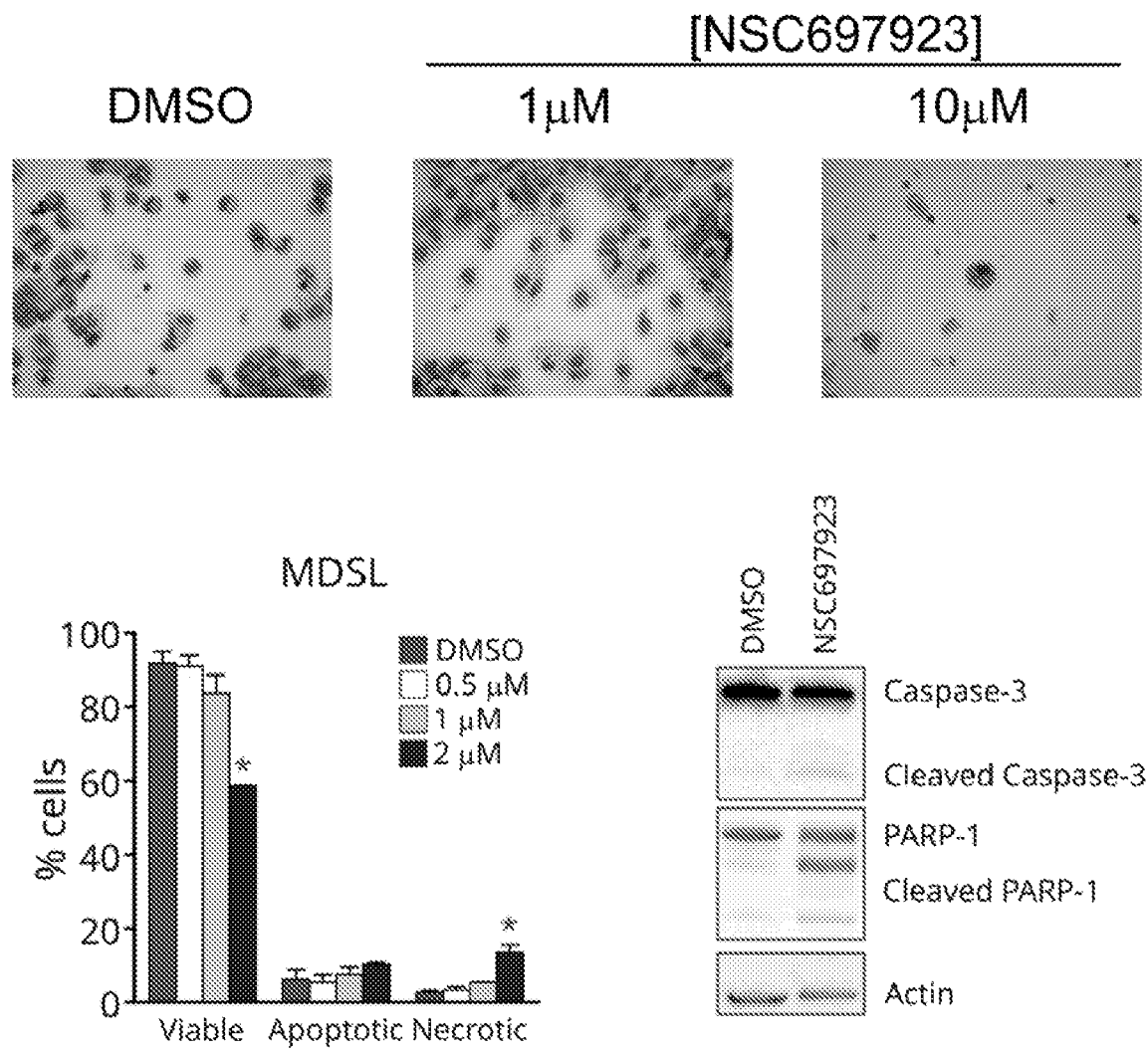
Figure 13:
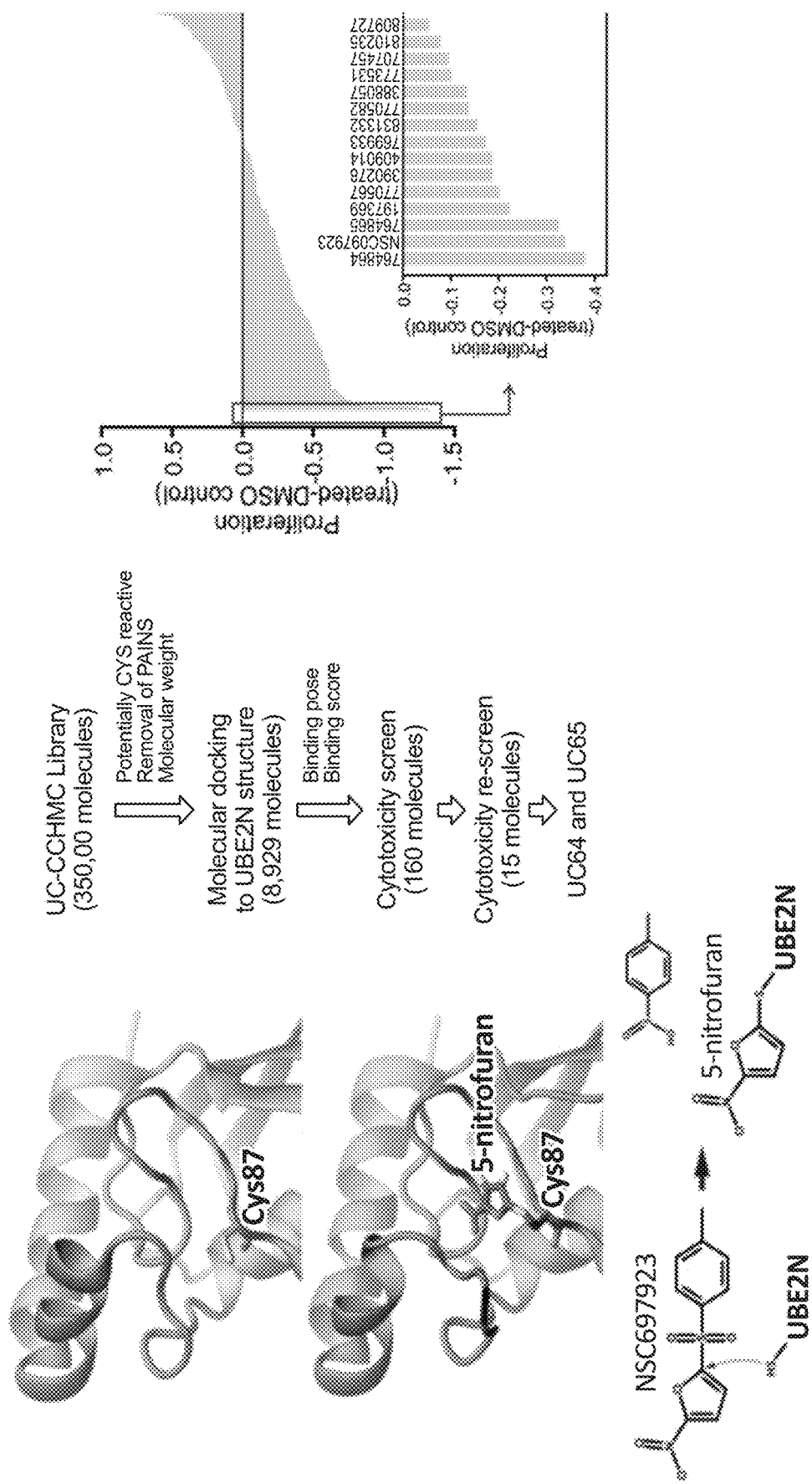
FIG. 13. Schematic of structure based in silico library screening to identify cysteine-reactive inhibitors of UBE2N FIG. 14. UC 64 and UC 65 directly bind UBE2N, through a Michael-Addition reaction.
Figure 14:
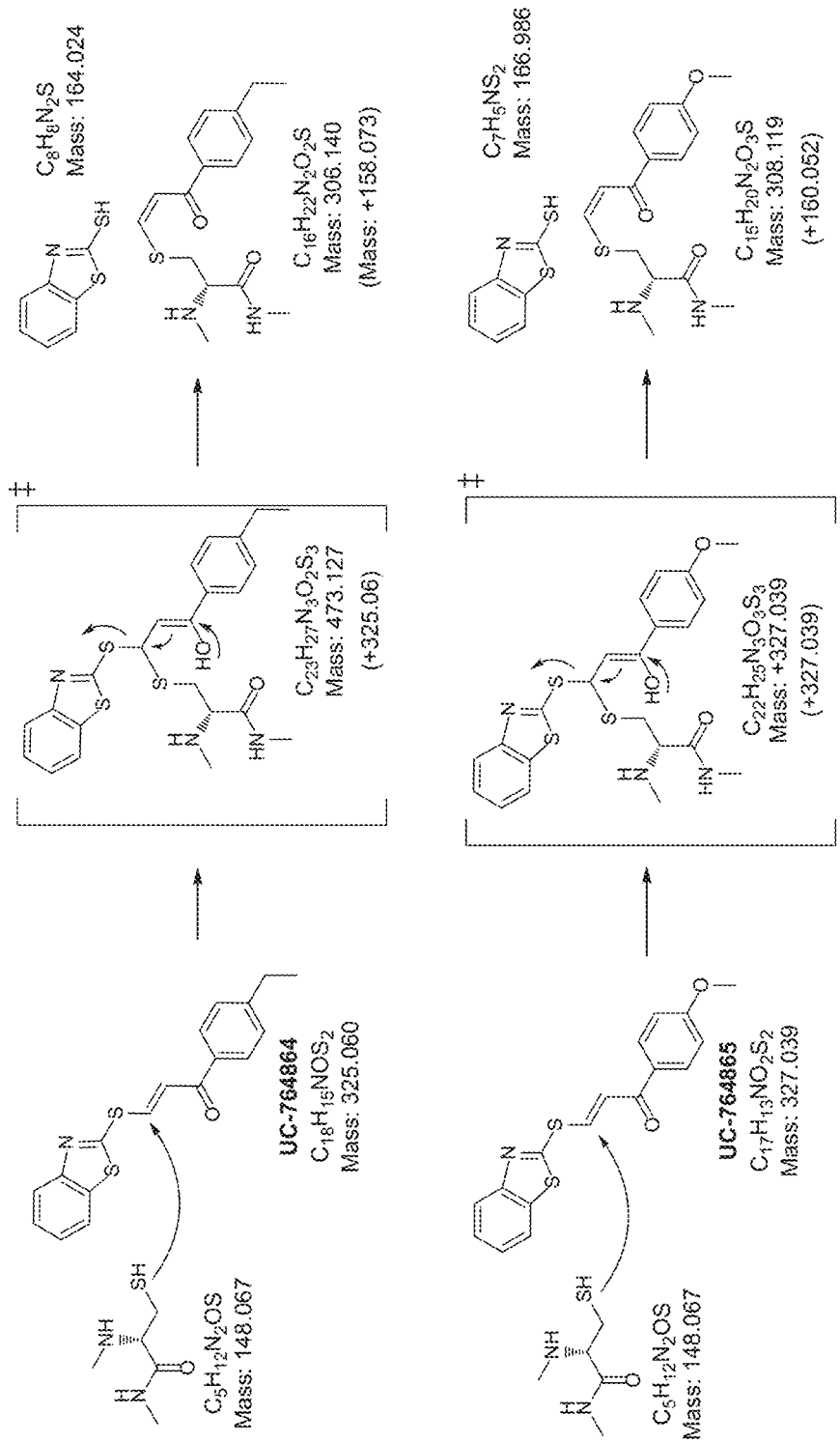
Figure 15:
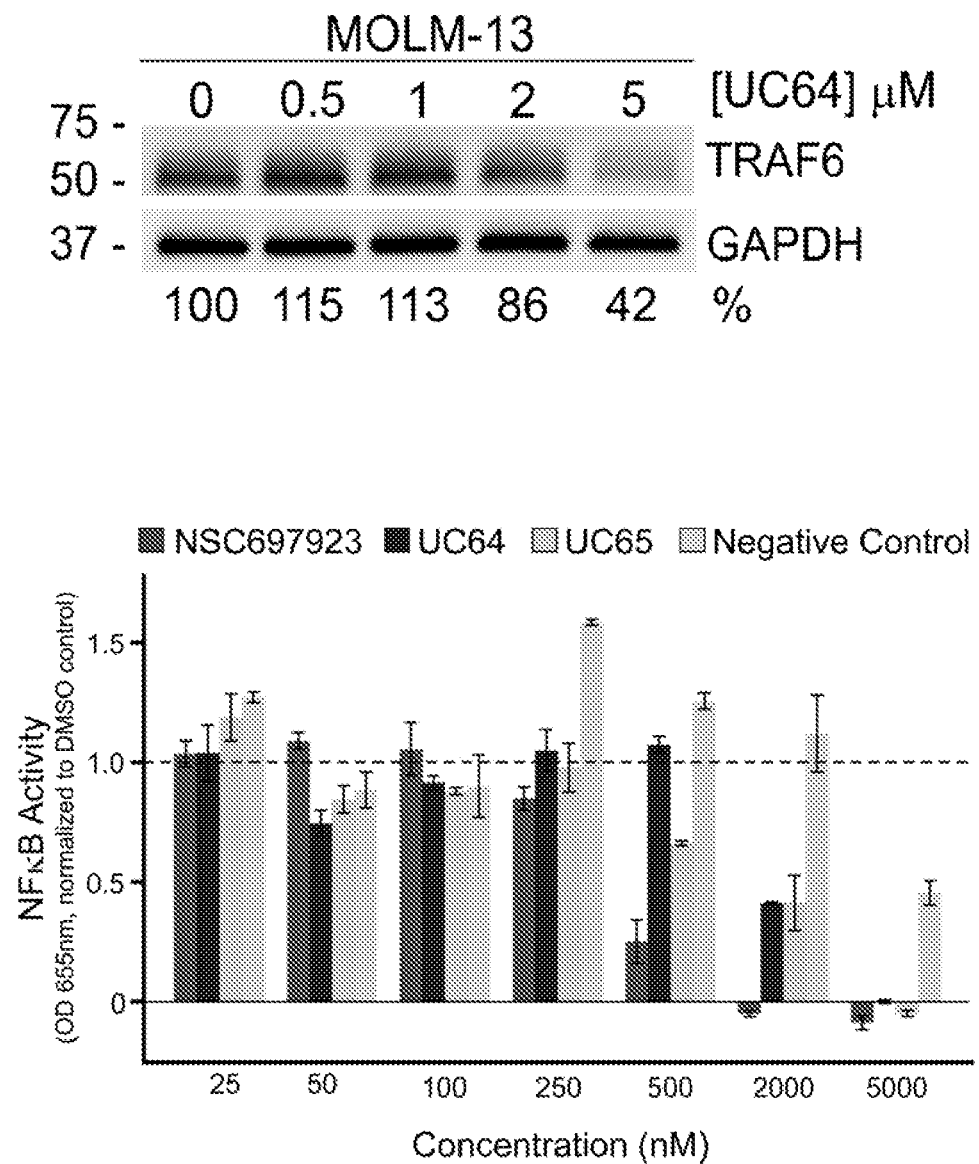
FIG. 15. Pharmacological inhibition of UBE2N with UC64 and UC65 inhibits NFkB signaling in AML cells.
Figure 16:
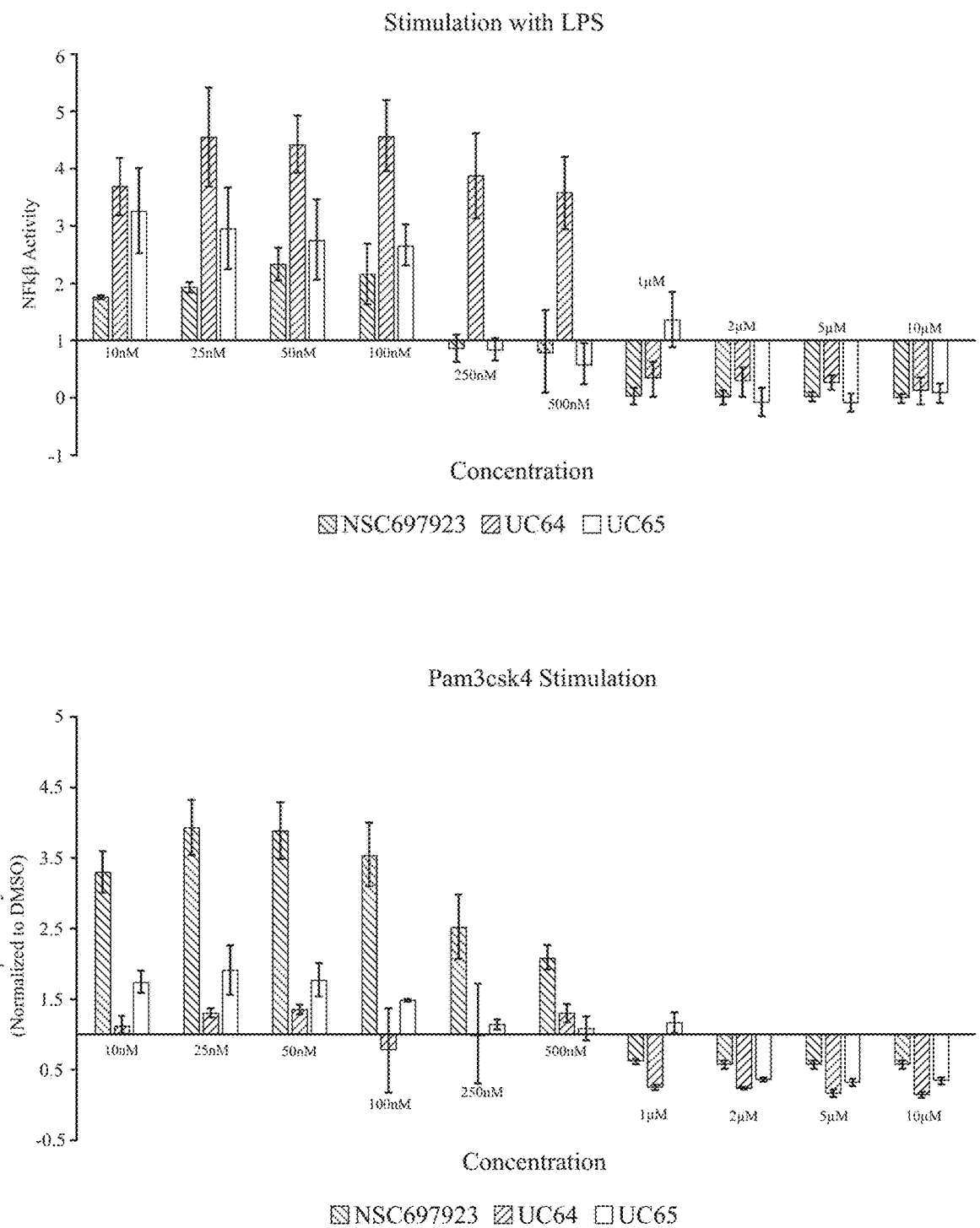
FIG. 16. Pharmacological inhibition of UBE2N with UC64 and UC65 inhibits TLR mediated NFkB signaling in AML cells.
Figure 17:
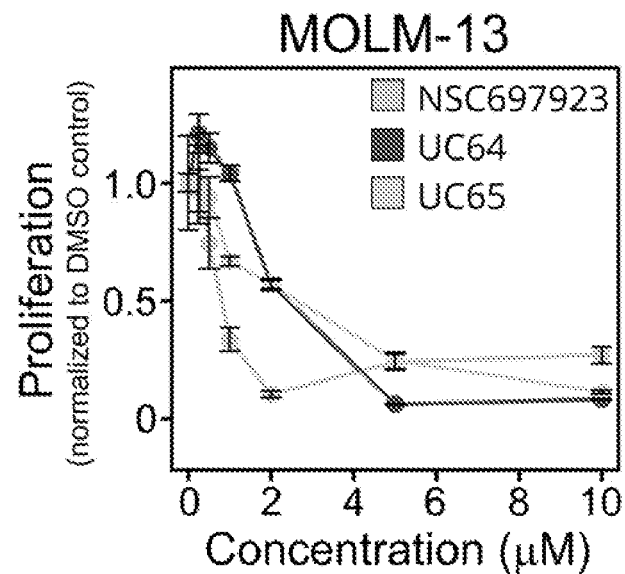
FIG. 17. Treatment of AML cells with UC64 and UC65 reduces their proliferation.
Figure 18:
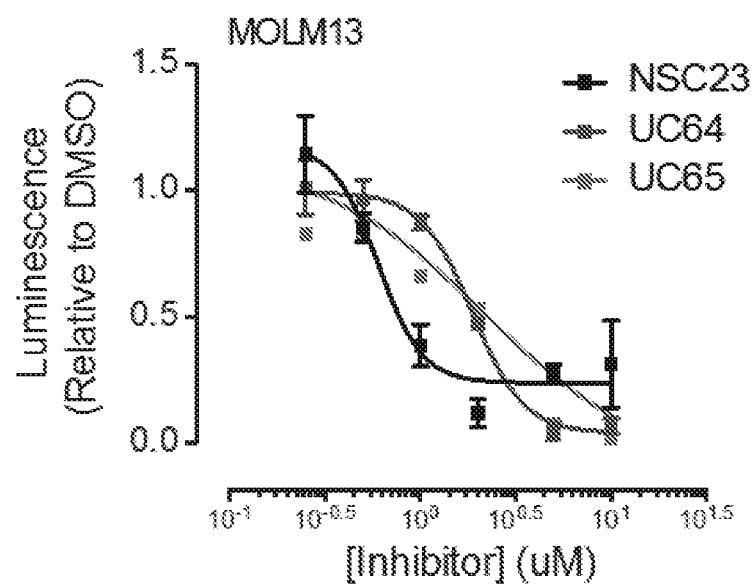
FIG. 18. Treatment of AML cells with UC64 and UC65 reduces their viability.
Figure 19:
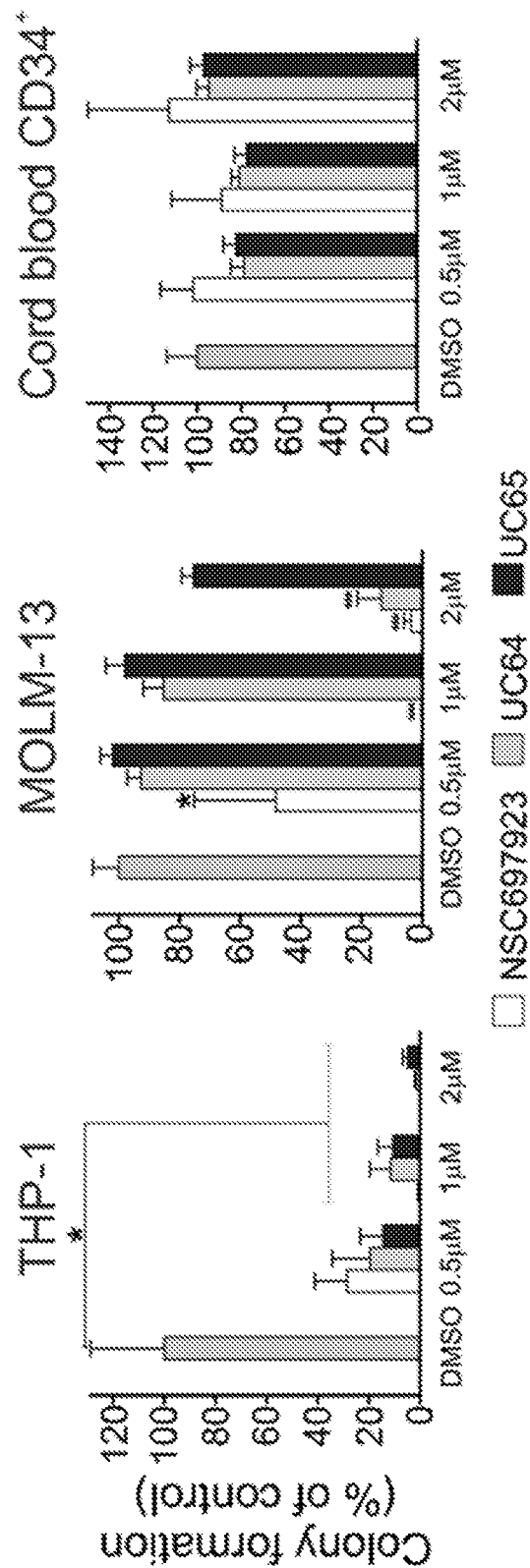
FIG. 19. Treatment of AML cells with UC64 and UC65 reduces their clonogenic potential.
Figure 20:
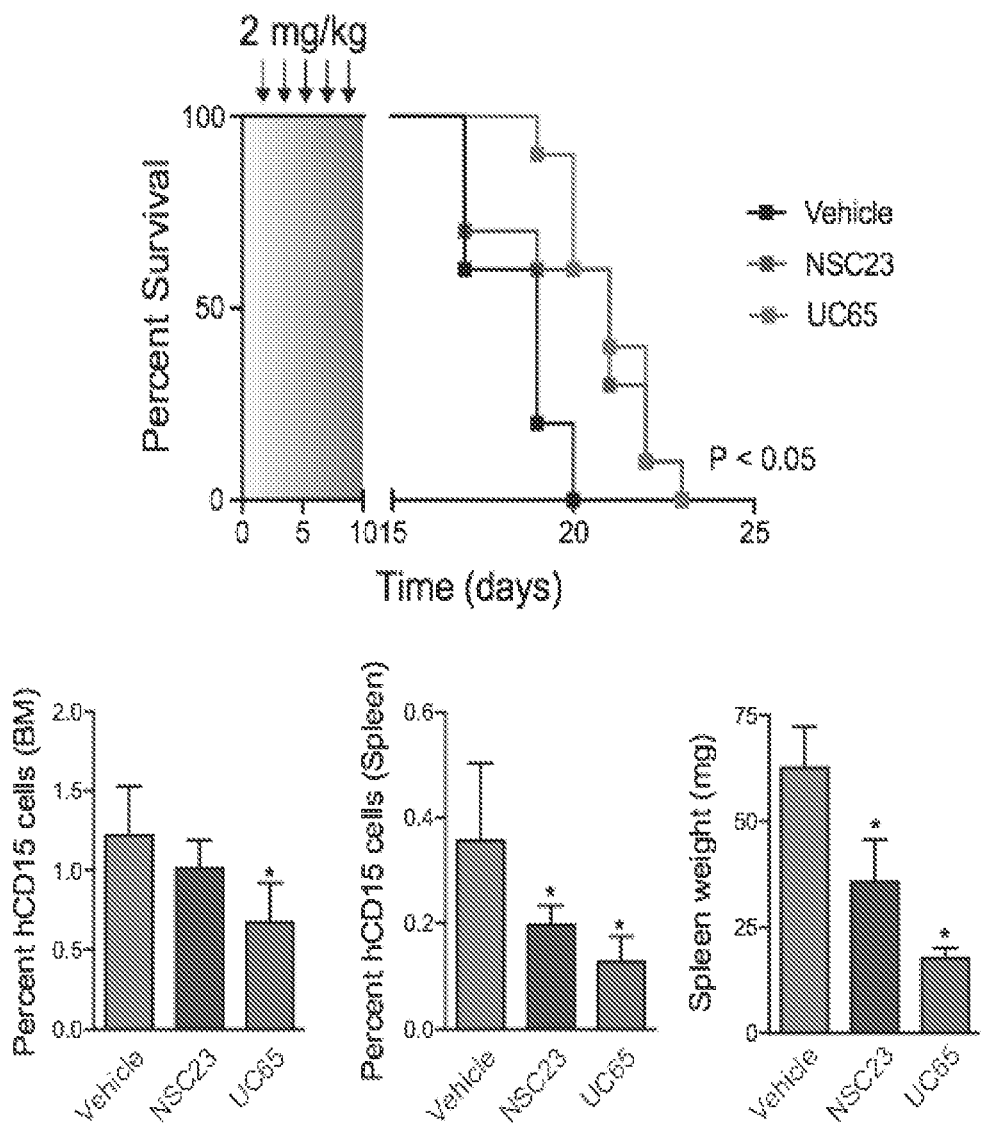
FIG. 20. UC65 is effective against targeting MDS/AML cells in vivo.
Figure 21:
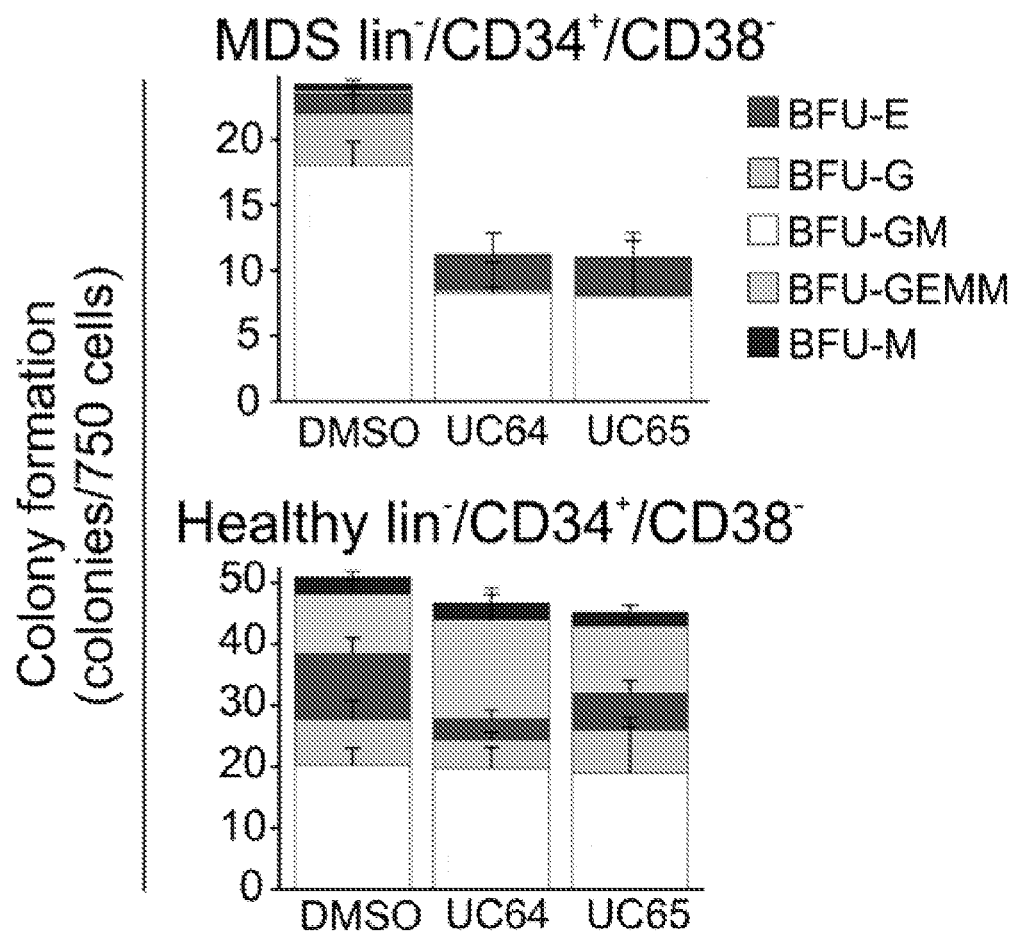
FIG. 21. Treatment of primary MDS stem cells with UC65/65 reduces their clonogenic potential.
Figure 22:
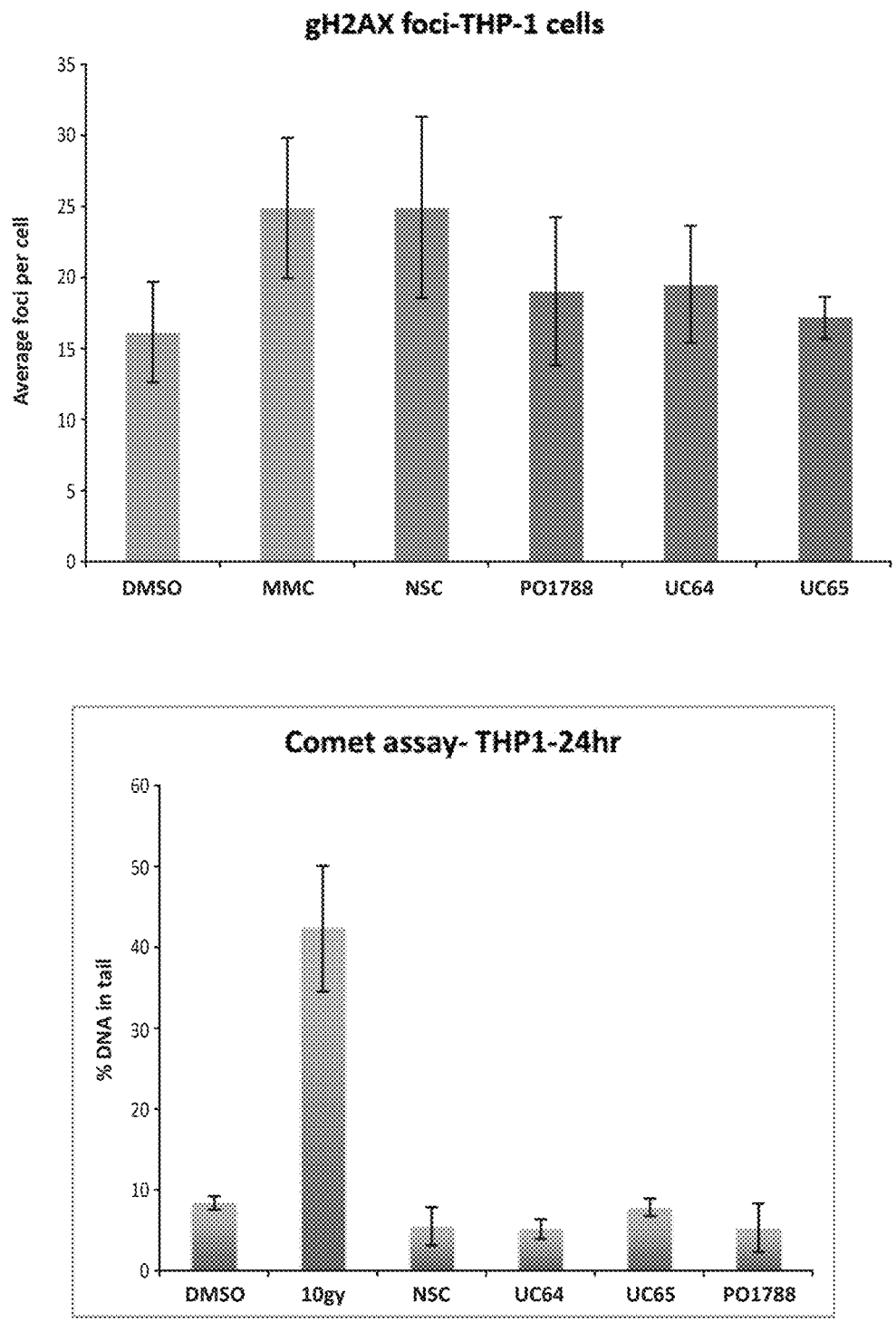
FIG. 22. Treatment of MOLM-13 and THP-1 cells with UC64/65 does not cause DNA damage.
Figure 23:
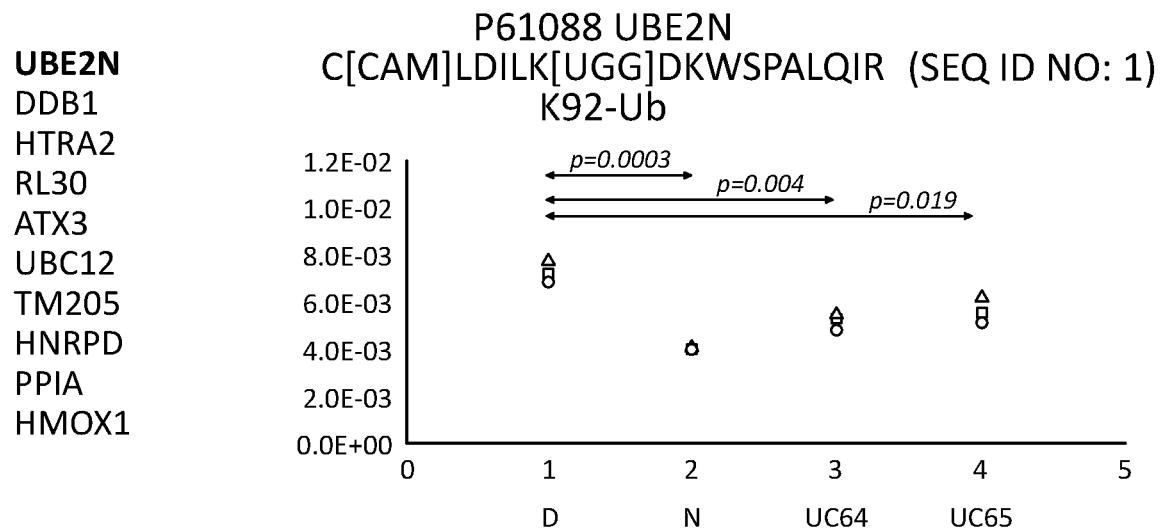
FIG. 23. UC64/65 reduces UBE2N ubiquination at Lysine (K)-92.
Figure 24:
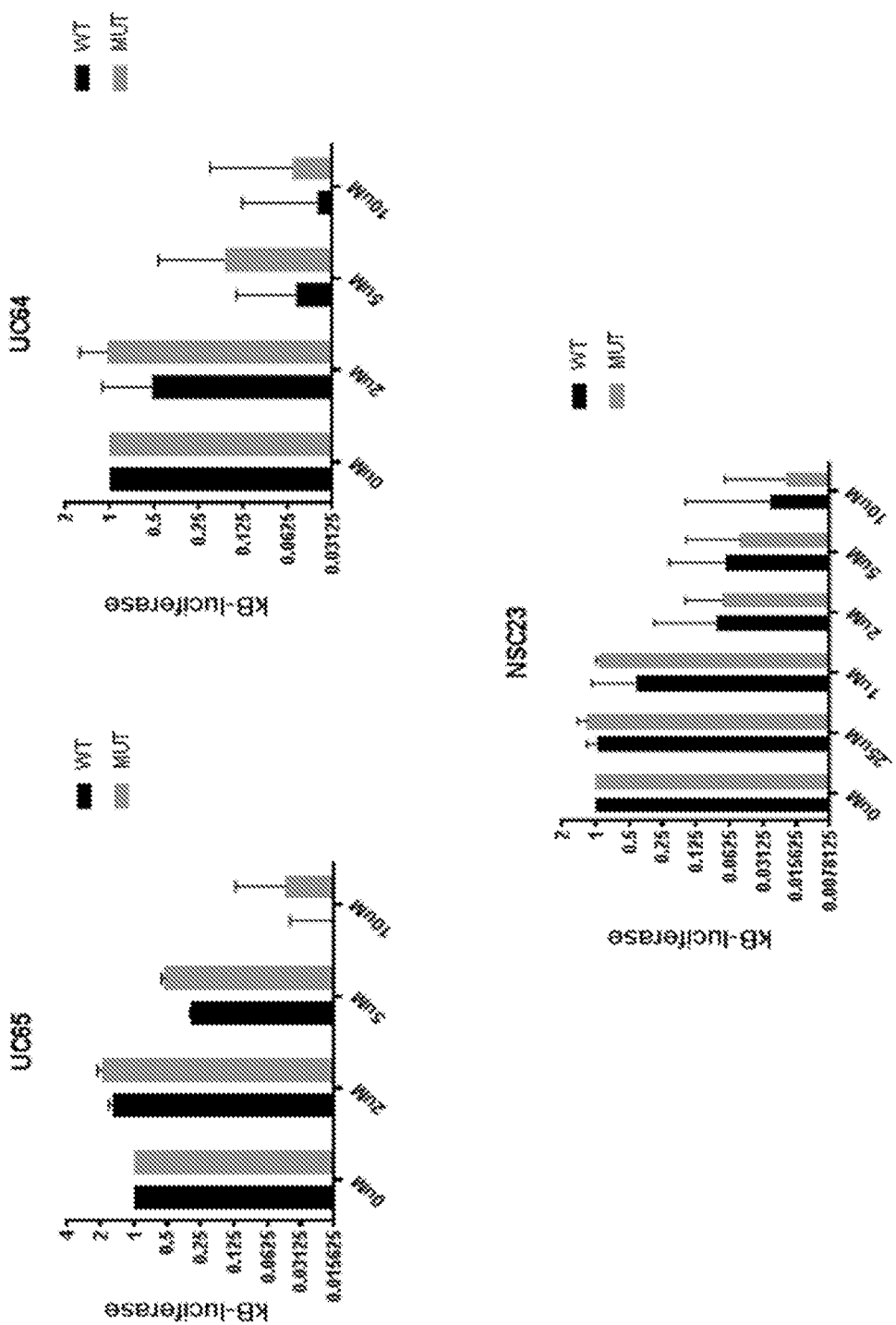
FIG. 24. UBE2N active site mutant is less sensitive to UC64/65 and NSC23 mediated inhibition of NFkB.
Figure 25:
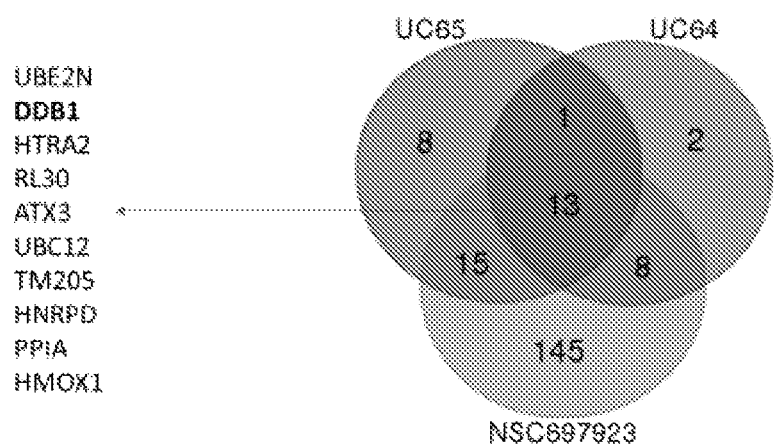
FIG. 25. DDB1 is differentially ubiquinated following inhibition of UBE2N with UC64/65 and NSC23.
Figure 26:
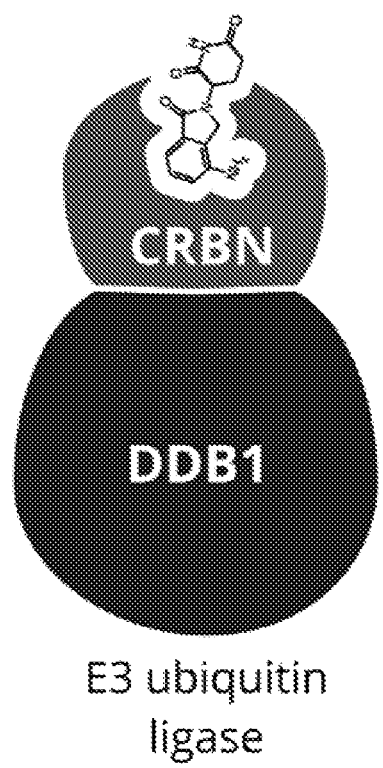
FIG. 26 is a schematic depicting DDB1, a component of the CUL4-CRBN E3 ligase complex targeted by lenalidomide.
Figure 27:
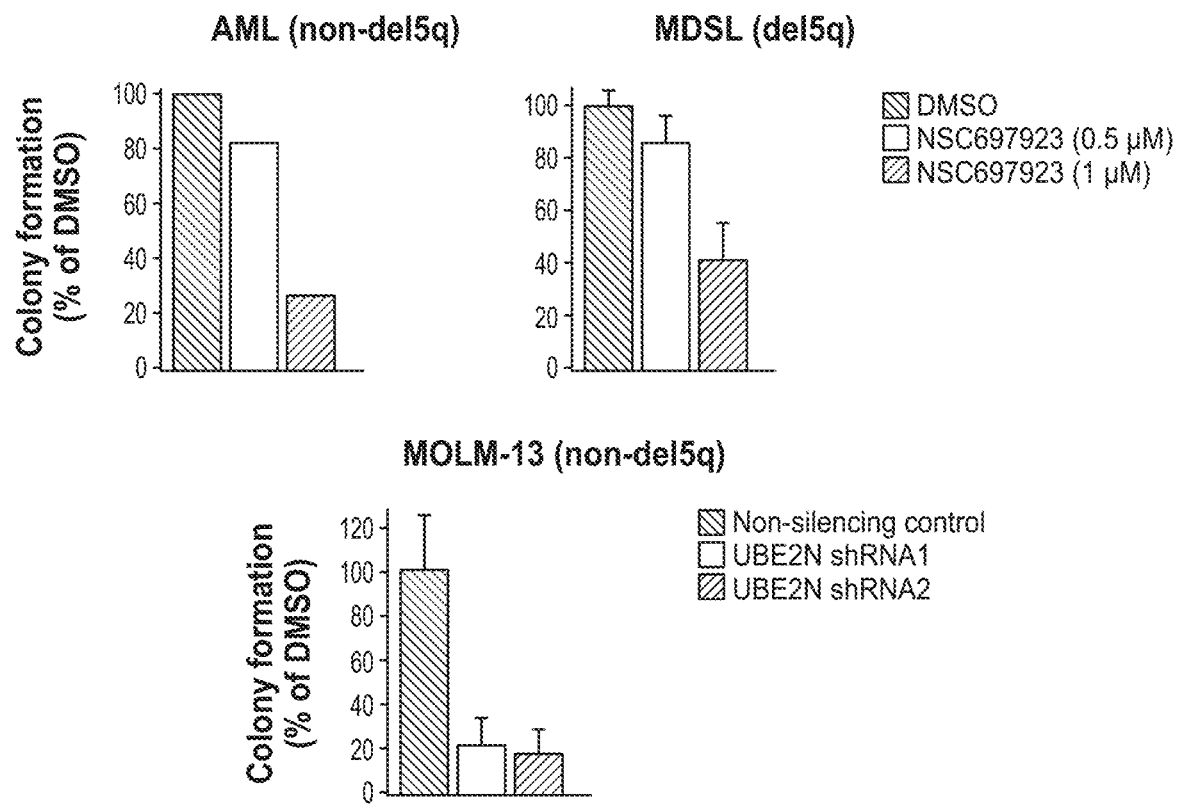
FIG. 27. UBE2N inhibition enhances the cytotoxic effects of lenalidomide in MDS/AML cells FIG. 28. UBE2N inhibition does not affect the function of normal CD34+ cells in the presence of lenalidomide.
Figure 28:
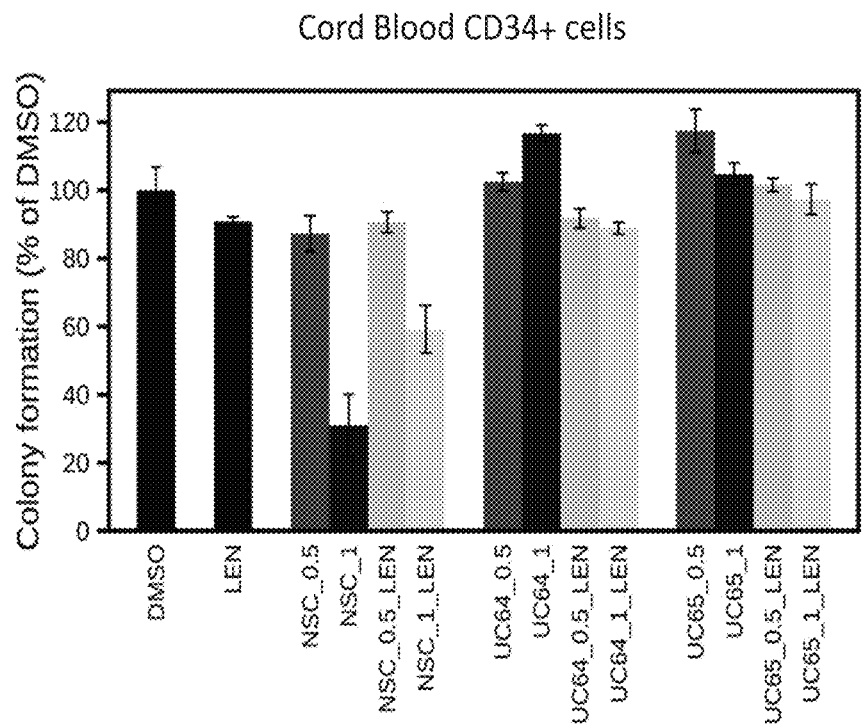
Figure 29:
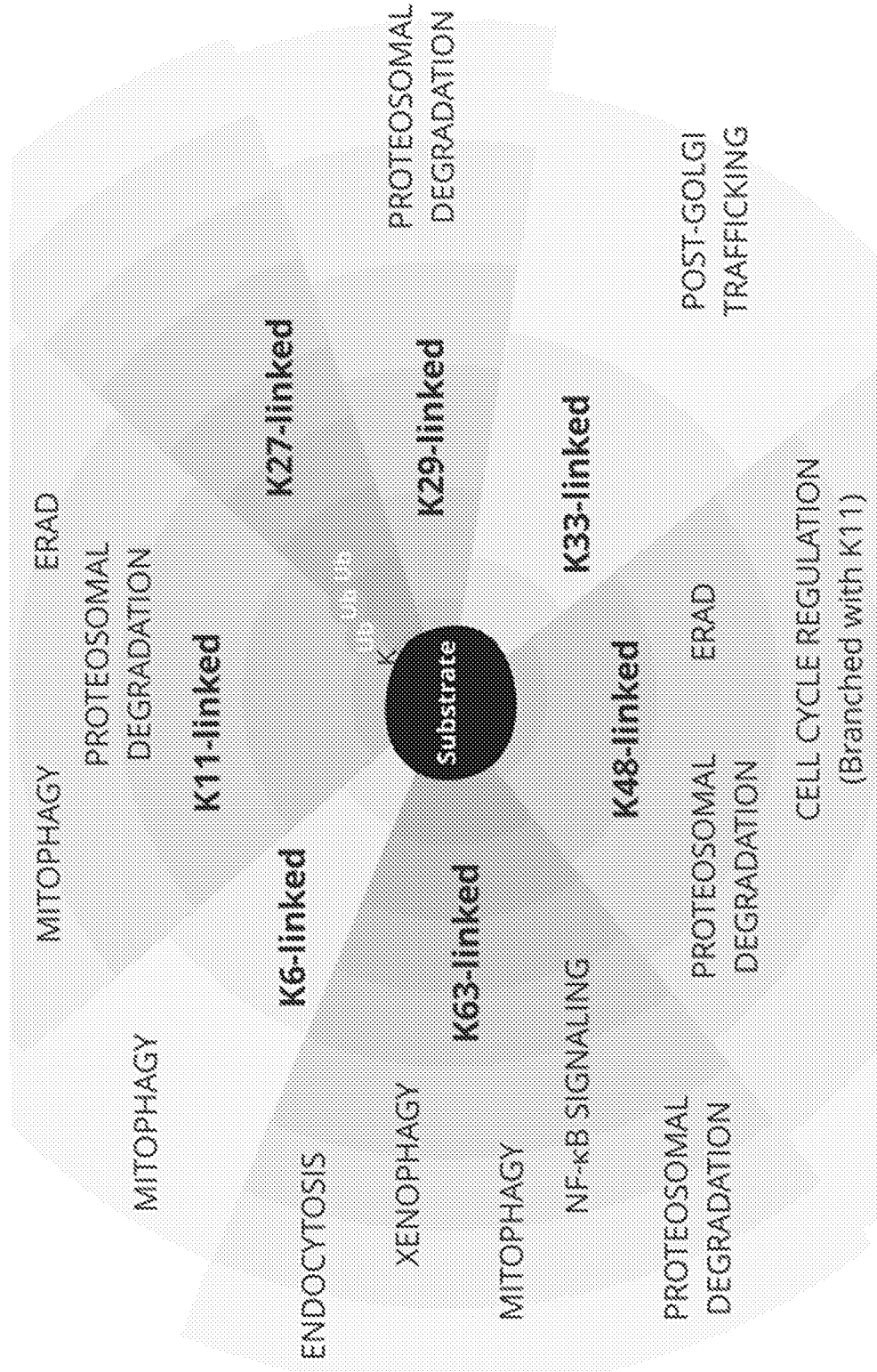
FIG. 29. Schematic of the forms of ubiquination.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms and expressions used herein have the ordinary meaning as is accorded to such terms and expressions with respect to their corresponding respective areas of inquiry and study except where specific meanings have otherwise been set forth herein.

The terms and expressions used herein have the ordinary meaning as is accorded to such terms and expressions with respect to their corresponding respective areas of inquiry and study except where specific meanings have otherwise been set forth herein.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms refer to children.

"Therapeutically effective amount" relates to the amount or dose of an active compound or composition described herein that will lead to one or more therapeutic effect, in particular, a desired beneficial effect. A therapeutically effective amount of a substance can vary according to factors such as the disease state, age, sex, and weight of the subject, and the ability of the substance to elicit a desired response in the subject. Dosage regime may be adjusted to provide the optimum therapeutic response. For example, several divided doses may be administered daily or the dose may be proportionally reduced as indicated by the exigencies of the therapeutic situation.

The phrase "pharmaceutically acceptable," as used in connection with compositions of the disclosure, refers to molecular entities and other ingredients of such compositions that are physiologically tolerable and do not typically produce untoward reactions when administered to a subject (e.g., human). In certain embodiments, as used herein, the term "pharmaceutically acceptable" means approved by a regulatory agency of a Federal or a state government or listed in the U.S. Pharmacopeia or other generally recognized pharmacopeia for use in mammals (e.g., humans).

The terms "pharmaceutically acceptable salts" or "a pharmaceutically acceptable salt thereof" refer to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts; salts of free acids and bases; inorganic salts, e.g., sulfate, hydrochloride, and hydrobromide; and other salts which are currently in widespread pharmaceutical use and are listed in sources well known to those of skill in the art, such as The Merck Index. Any suitable constituent can be selected to make a salt of an active drug discussed herein, provided that it is non-toxic and does not substantially interfere with the desired activity. In addition to salts, pharmaceutically acceptable precursors and derivatives of the compounds can be employed. Pharmaceutically acceptable amides, lower alkyl esters, and protected derivatives of the disclosed actives can also be suitable for use in the compositions and methods disclosed herein. A salt of a compound of this disclosure may be formed between an acid and a basic group of the compound, such as an amino functional group, or a base and an acidic group of the compound, such as a carboxyl functional group. According to another embodiment, the compound is a pharmaceutically acceptable acid addition salt. Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The terms "treat," "treating" or "treatment," as used herein, refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

The term "carrier" applied to pharmaceutical compositions of the disclosure refers to a diluent, excipient, or vehicle with which an active compound is administered. Such pharmaceutical carriers can be sterile liquids, such as water, saline solutions, aqueous dextrose solutions, aqueous glycerol solutions, and oils, including those of petroleum, animal, vegetable, or synthetic origin, such as peanut oil, soybean oil, mineral oil, sesame oil and the like. Suitable pharmaceutical carriers are described in "Remington's Pharmaceutical Sciences" (any edition).

The term "compound," as used herein, is also intended to include any salts, solvates, or hydrates thereof.

Applicant has discovered novel methods of treating a myelodyspastic syndrome (MDS) and/or an acute myeloid leukemia (AML), which may include administration of one or more of the disclosed compounds/compositions to an individual in need thereof.

In some embodiments, the method of treating a myelodyspastic syndrome (MDS) and/or an acute myeloid leukemia (AML) may comprise the step of administering one or more compounds selected from:

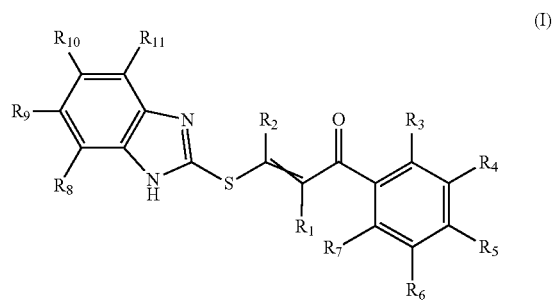

(I)

wherein $R_1$ is selected from H, F, Cl, Br, nitrile, $CH_3$, and $CH_2CH_3$; $R_2$ is selected from H, F, Cl, and $C_1$-$C_4$ alkyl; $R_3$-$R_7$ are independently selected from H, F, Cl, Br, nitrile, $NHCOCH_3$, $C_1$-$C_4$ alkyl, $C_1$-$C_4$ alkoxy; and $R_4$ with either $R_3$ or $R_5$ are a substituted or unsubstituted benzo fused ring; and $R_8$-$R_{10}$ are independently selected from H, F, Cl, Br, nitrile $NHCOCH_3$, $C_1$-$C_4$ alkyl, $C_1$-$C_4$ alkoxy. Compound (I) is an alpha, beta unsaturated ketone with a 2-mercaptobenzimidazole at the beta position. The double bond may be cis or trans. In some embodiments, the double bond is trans.

In some embodiments, for Compound 1, $R_1$, $R_2$, $R_3$, $R_4$, $R_6$, $R_7$, $R_8$, $R_{10}$, and $R_{11}$ are H; and $R_5$ and $R_9$ are independently selected from H, F, Cl, Br, nitrile $NHCOCH_3$, $C_1$-$C_4$ alkyl, $C_1$-$C_4$ alkoxy. Examples include, but are not limited to:

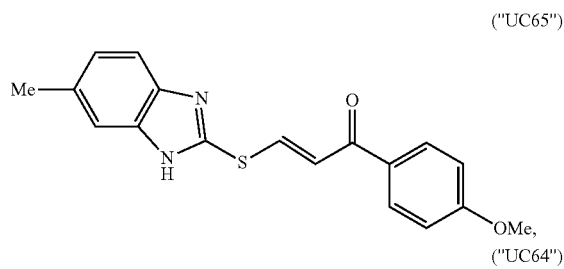

("UC65")

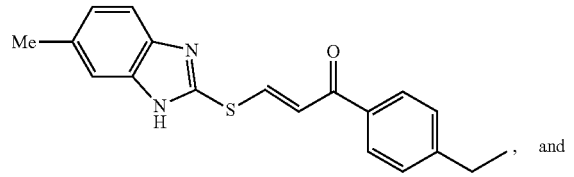

("UC64")

, and

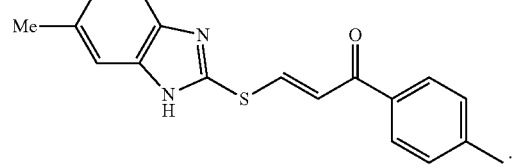

.

In one aspect, the method of treating a myelodyspastic syndrome (MDS) and/or an acute myeloid leukemia (AML) may comprise the step of administering one or more compounds selected from:

(Compound I)

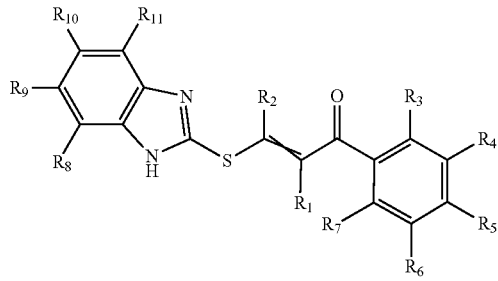

wherein $R_1$ is selected from H, F, Cl, Br, nitrile, $CH_3$, and $CH_2CH_3$; $R_2$ is selected from H, F, Cl, and $C_1$-$C_4$ alkyl; $R_3$-$R_7$ are independently selected from H, F, Cl, Br, nitrile, $NHCOCH_3$, $C_1$-$C_4$ alkyl, $C_1$-$C_4$ alkoxy; and $R_4$ with either $R_3$ or $R_5$ are a substituted or unsubstituted benzo fused ring; and $R_8$-$R_{10}$ are independently selected from H, F, Cl, Br, nitrile $NHCOCH_3$, $C_1$-$C_4$ alkyl, $C_1$-$C_4$ alkoxy, wherein Compound I does not include

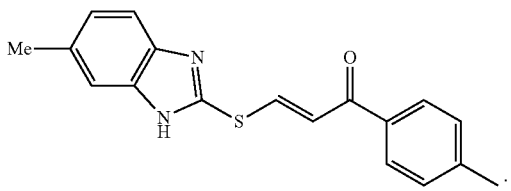 [SMILES: Cc1ccc(C(=O)/C=C/Sc2nc3ccc(C)cc3[nH]2)cc1]

In some embodiments, for Compound 1, $R_1$, $R_2$, $R_3$, $R_4$, $R_6$, $R_7$, $R_8$, $R_{10}$, and Ru are H; and $R_5$ and $R_9$ are independently selected from H, F, Cl, Br, nitrile $NHCOCH_3$, methyl, ethyl, methoxy and ethoxy.

In some embodiments, the compound is selected from:

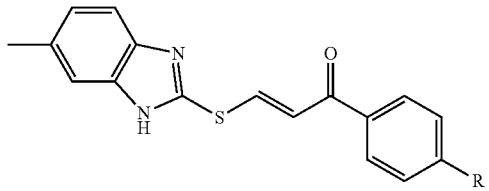

wherein R is selected from ethyl and methoxy.

The term "alkyl" includes straight, branched chain, or cyclic alkyl groups, such as, but not limited to, methyl, ethyl, propyl, butyl, trifluoromethyl, and tetradecyl.

The term "alkoxy" includes straight, branched chain, or cyclic alkoxy groups, such as, but not limited to, methoxy, ethoxy, propoxy, butoxy, 2-methoxyethoxy, sec-butoxy, hexyloxy, and 2-ethylhexyloxy, tetradecyloxy groups.

The term "group" is used, it is intended to encompass not only the substituent's unsubstituted form, but also its form further substituted with any substituent group or groups as herein mentioned, so long as the substituent does not destroy properties necessary for utility. Suitably, a substituent group may be halogen or may be bonded to the remainder of the molecule by an atom of carbon, nitrogen, oxygen, or sulphur.

In one aspect, the method of treating a myelodyspastic syndrome (MDS) and/or an acute myeloid leukemia (AML) may comprise the step of administering the compound ("Bay 11-7082)

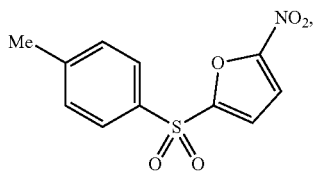

alone or in combination with a compound described herein, to an individual in need thereof.

In one aspect, the method of treating a myelodyspastic syndrome (MDS) and/or an acute myeloid leukemia (AML) may comprise the step of administering the compound (NSC697923)

alone or in combination with a compound described herein, to an individual in need thereof.

In one aspect, the one or more compounds may be administered in an amount sufficient to activate TRAF6 and/or NF kappa beta.

In one aspect, the one or more compounds may be administered in an amount sufficient to slow or prevent growth of AML and/or MDS cells, reduce clonogenic potential of AML and/or MDS cells, reduce AML and/or MDS cell viability; promote apoptosis of AML and/or MDS cells, or combinations thereof.

In one aspect, the one or more compounds may be co-administered with lenalidomide ("LEN"), wherein said administration is in an amount sufficient to reduce/inhibit MDS/AML cell function.

In one aspect, the one or more compounds may be co-administered with a chemotherapeutic agent selected from a taxane, a platinum-based agent, an anthracycline, an alkylating agent, a vinca alkaloid, an epothilone, a histone deacetylase inhibitor, a topoisomerase I and II inhibitor, a kinase inhibitor, a nucleotide analog, a precursor analog, a peptide antibiotic, and combinations thereof In one aspect, a method of treating a non-del(5q) MDS patient is disclosed, in which an individual is administered a compound or compositions as disclosed herein.

In one aspect, an article of manufacture is disclosed, in which the article of manufacture may comprise a container, a composition or compound as disclosed herein in a dosage form, and instructions for administering said dosage form to an individual diagnosed or suspected of having a myelodysplastic syndrome (MDS) and/or an acute myeloid leukemia (AML). The dosage form may be any disclosed herein, for example, an oral dosage form, a form suitable for bronchial administration, or an intravenous form. The article of manufacture may further comprise a means for delivery of said dosage form.

Dosage

In one aspect, an agent disclosed herein may be present in an amount of from about 0.5% to about 95%, or from about 1% to about 90%, or from about 2% to about 85%, or from about 3% to about 80%, or from about 4%, about 75%, or from about 5% to about 70%, or from about 6%, about 65%, or from about 7% to about 60%, or from about 8% to about 55%, or from about 9% to about 50%, or from about 10% to about 40%, by weight of the composition.

The compositions may be administered in oral dosage forms such as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, intralesional, or intramuscular forms all utilizing dosage forms well known to those of ordinary skill in the pharmaceutical arts. The compositions may be administered by intranasal route via topical use of suitable intranasal vehicles, or via a transdermal route, for example using conventional transdermal skin patches. A dosage protocol for administration using a transdermal delivery system may be continuous rather than intermittent throughout the dosage regimen.

In one aspect, the compounds may be administered at the rate of 100 µg to 1000 mg per day per kg of body weight. Orally, the compounds may be suitably administered at the rate of about 100, 150, 200, 250, 300, 350, 400, 450, or 500 µg to about 1, 5, 10, 25, 50, 75, 100, 200, 300, 400, 500, 600, 700, 800, 900, 1000 mg per day per kg of body weight. The required dose can be administered in one or more portions. For oral administration, suitable forms are, for example, tablets, gel, aerosols, pills, dragees, syrups, suspensions, emulsions, solutions, powders and granules; one method of administration includes using a suitable form containing from 1 mg to about 500 mg of active substance. In one aspect, administration may comprise using a suitable form containing from about 1, 2, 5, 10, 25, or 50 mg to about 100, 200, 300, 400, 500 mg of active substance.

A dosage regimen will vary depending upon known factors such as the pharmacodynamic characteristics of the agents and their mode and route of administration; the species, age, sex, health, medical condition, and weight of the patient, the nature and extent of the symptoms, the kind of concurrent treatment, the frequency of treatment, the route of administration, the renal and hepatic function of the patient, and the desired effect. The effective amount of a drug required to prevent, counter, or arrest progression of a symptom or effect of a muscle contracture can be readily determined by an ordinarily skilled physician The pharmaceutical compositions may include suitable dosage forms for oral, parenteral (including subcutaneous, intramuscular, intradermal and intravenous), transdermal, sublingual, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. Oral preparations include push-fit capsules made of gelatin, as well as soft, scaled capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. For topical or nasal administration, penetrants or permeation agents that are appropriate to the particular barrier to be permeated are used in the formulation. Such penetrants are generally known in the art. The pharmaceutical compositions are prepared by conventional techniques appropriate to the desired preparation containing appropriate amounts of the active ingredient, that is, one or more of the disclosed active agents or a pharmaceutically acceptable salt thereof according to the invention.

The dosage of an agent disclosed herein used to achieve a therapeutic effect will depend not only on such factors as the age, weight and sex of the patient and mode of administration, but also on the degree of inhibition desired and the potency of an agent disclosed herein for the particular disorder or disease concerned. It is also contemplated that the treatment and dosage of an agent disclosed herein may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

Routes of Administration

Any suitable route of administration can be employed for providing the patient with an effective dosage of the disclosed compositions. For example, oral, rectal, transdermal, parenteral (subcutaneous, intramuscular, intravenous), intrathecal, topical, inhalable, and like forms of administration can be employed. Suitable dosage forms include tablets, troches, dispersions, suspensions, solutions, capsules, patches, and the like. Administration of medicaments prepared from the compounds described herein can be by any suitable method capable of introducing the compounds into the bloodstream. In some embodiments, the formulations can contain a mixture of active compounds with pharmaceutically acceptable carriers or diluents known to those of skill in the art.

The compositions can be prepared in any desired form, for example, tables, powders, capsules, injectables, suspensions, sachets, cachets, patches, solutions, elixirs, and aerosols. Carriers such as starches, sugars, microcrystalline cellulose, diluents, granulating agents, lubricants, binders, disintegrating agents, and the like can be used in oral solid preparations. In certain embodiments, the compositions are prepared as oral solid preparations (such as powders, capsules, and tablets). In certain embodiments, the compositions are prepared as oral liquid preparations. In some embodiments, the oral solid preparations are tablets. If desired, tablets can be coated by standard aqueous or non-aqueous techniques.

In addition to the dosage forms set out above, one or more disclosed compounds may also be administered by sustained release, delayed release, or controlled release compositions and/or delivery devices.

Pharmaceutical compositions suitable for oral administration can be provided as discrete units such as capsules, cachets, sachets, patches, injectables, tablets, and aerosol sprays, each containing predetermined amounts of the active ingredients, as powder or granules, or as a solution or a suspension in an aqueous liquid, a non-aqueous liquid, an oil-in-water emulsion, or a water-in-oil liquid emulsion. Such compositions can be prepared by any of the conventional methods of pharmacy, and may include the step of bringing into association the active ingredients with a carrier which constitutes one or more ingredients. In general, the compositions may be prepared by uniformly and intimately admixing the active ingredients with liquid carriers, finely divided solid carriers, or both, and then, optionally, shaping the product into the desired presentation.

For example, a tablet can be prepared by compression or molding, optionally, with one or more additional ingredients. Compressed tablets can be prepared by compressing in a suitable machine the active ingredient in a free-flowing form such as powder or granules, optionally mixed with a binder, lubricant, inert diluent, surface active or dispersing agent. Molded tablets can be made by molding, in a suitable machine, a mixture of the powdered compound moistened with an inert liquid diluent.

A composition or formulation may be administered to a subject continuously or periodically.

The compositions or fractions thereof typically comprise suitable pharmaceutical diluents, excipients, vehicles, or carriers selected based on the intended form of administration, and consistent with conventional pharmaceutical practices. The carriers, vehicles etc. may be adapted to provide an additive, synergistically effective or therapeutically effective amount of the active compounds. Suitable pharmaceutical diluents, excipients, vehicles, and carriers are described in the standard text, Remington: The Science and Practice of Pharmacy, and in The United States Pharmacopeia: The National Formulary (USP 24 NF 19) published in 1999. By way of example, for oral administration in the form of a capsule or tablet, the active components can be combined with an oral, non-toxic pharmaceutically acceptable inert carrier such as lactose, starch, sucrose, methyl cellulose, magnesium stearate, glucose, calcium, sulfate, dicalcium phosphate, mannitol, sorbital, and the like. For oral administration in a liquid form, the agents may be combined with any oral, non-toxic, pharmaceutically acceptable inert carrier such as ethanol, glycerol, water, and the like. Suitable binders (e.g. gelatin, starch, corn sweeteners, natural sugars including glucose; natural and synthetic gums, and waxes), lubricants (e.g. sodium oleate, sodium stearate, magnesium stearate, sodium benzoate, sodium acetate, and sodium chloride), disintegrating agents (e.g. starch, methyl cellulose, agar, bentonite, and xanthan gum), flavoring agents, and coloring agents may also be combined in the compositions or components thereof.

In one aspect, a pharmaceutical composition may have pH from about 7 to 10.

Formulations for parenteral administration of a composition may include aqueous solutions, syrups, aqueous or oil suspensions and emulsions with edible oil such as cottonseed oil, coconut oil or peanut oil. Dispersing or suspending agents that can be used for aqueous suspensions include synthetic or natural gums, such as tragacanth, alginate, acacia, dextran, sodium carboxymethylcellulose, gelatin, methylcellulose, and polyvinylpyrrolidone.

Compositions for parenteral administration may include sterile aqueous or non-aqueous solvents, such as water, isotonic saline, isotonic glucose solution, buffer solution, or other solvents conveniently used for parenteral administration of therapeutically active agents. A composition intended for parenteral administration may also include conventional additives such as stabilizers, buffers, or preservatives.

In an embodiment, a solid form pharmaceutical composition is provided (e.g. tablets, capsules, powdered, or pulverized form) comprising one or more disclosed compounds or salt thereof.

After pharmaceutical compositions have been prepared, they can be placed in an appropriate container and labeled for treatment of an indicated condition. For administration of a composition, such labeling would include amount, frequency, and method of administration.

Kits

Kits are also provided. In one aspect, a kit may comprise or consist essentially of agents or compositions described herein. The kit may be a package that houses a container which may contain a composition comprising an oxime or pharmaceutically acceptable salt thereof as disclosed herein, and also houses instructions for administering the agent or composition to a subject. In one aspect, a pharmaceutical pack or kit is provided comprising one or more containers filled with one or more composition as disclosed herein. Associated with such container(s) can be various written materials such as instructions for use, or a notice in the form prescribed by a governmental agency regulating the manufacture, use or sale of pharmaceuticals or biological products, which notice reflects approval by the agency of manufacture, use, or sale for human administration.

As there may be advantages to mixing a component of a composition described herein and a pharmaceutically acceptable carrier, excipient or vehicle near the time of use, kits in which components of the compositions are packaged separately are disclosed. For example, the kit can contain an active ingredient in a powdered or other dry form in, for example, a sterile vial or ampule and, in a separate container within the kit, a carrier, excipient, or vehicle, or a component of a carrier, excipient, or vehicle (in liquid or dry form). In one aspect, the kit can contain a component in a dry form, typically as a powder, often in a lyophilized form in, for example, a sterile vial or ampule and, in a separate container within the kit, a carrier, excipient, or vehicle, or a component of a carrier, excipient, or vehicle. Alternatively, the kit may contain a component in the form of a concentrated solution that is diluted prior to administration. Any of the components described herein, any of the carriers, excipients or vehicles described herein, and any combination of components and carriers, excipients or vehicles can be included in a kit.

Optionally, a kit may also contain instructions for preparation or use (e.g., written instructions printed on the outer container or on a leaflet placed therein) and one or more devices to aid the preparation of the solution and/or its administration to a patient (e.g., one or a plurality of syringes, needles, filters, tape, tubing, alcohol swabs, or the like). Compositions which are more concentrated than those administered to a subject can be prepared. Accordingly, such compositions can be included in the kits with, optionally, suitable materials (e.g., water, saline, or other physiologically acceptable solutions) for dilution. Instructions included with the kit can include, where appropriate, instructions for dilution.

In other embodiments, the kits can include pre-mixed compositions and instructions for solubilizing any precipitate that may have formed during shipping or storage. Kits containing solutions of one or more of the aforementioned active agents, or pharmaceutically acceptable salts thereof, and one or more carriers, excipients or vehicles may also contain any of the materials mentioned above (e.g., any device to aid in preparing the composition for administration or in the administration per se). The instructions in these kits may describe suitable indications (e.g., a description of patients amenable to treatment) and instructions for administering the solution to a patient.

Examples

Applicant has found that UBE2N inhibition achieves reduction of TRAF6 protein levels, abrogation of TRAF6 signaling in AML/MDS cell lines and primary cells, AML/MDS cell cycle arrest (leading to cell death); alteration of upiquitination of DDDB1 (a component of the CRBN complex), and cooperation with lenalidomide to reduce AML/MDS cell function. Net, the data reveals that UBE2N, an E2 ubiquitin conjugating enzyme, as a novel therapeutic target in MDS/AML.

Hematopoietic stem and progenitor cells (HSPC) from MDS and AML patients exhibit overexpression of TRAF6 and related innate immune pathway genes, suggesting a dependency of leukemic HSPC on activated innate immune signaling. Unfortunately, inhibiting TRAF6 directly has proven difficult, as few binding pockets on TRAF6 exist for targeting small molecules. UBE2N/Ubc13, a cofactor of TRAF6 and key enzyme in innate immune signaling, is a ubiquitin-conjugating E2 enzyme that catalyzes lysine 63 (K63)-linked ubiquitin chains on GRAF6 and its substrates. Importantly, a commercially available compound and a chemical series of UBE2N inhibitors are available. Applicant evaluated the cellular and molecular effects of pharmacologic and genetic inhibition of UBE2N in MDS and AML cells.

Pharmacological inhibition of UBE2N with NSC697923 (available from Sigma Aldrich, Tocris, Cayman, and other vendors), having the following structure:

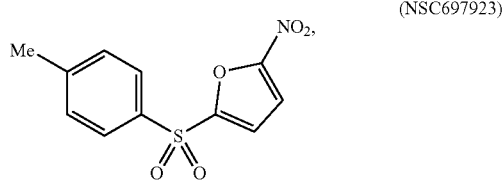 [SMILES: Cc1ccc(S(=O)(=O)c2ccc([N+](=O)[O-])o2)cc1]

(NSC697923)

or genetic inhibition with shRNAs reduced the clonogenic capacity of MDSL/AML cell lines and primary cells while not significantly affecting normal HSPC. Treatment of MDS/AML cells with NSC697923 reduced the cellular metabolic activity, induced a G2/M cell cycle arrest, and increased cell death. Moreover, xenotransplantation of an MDS-derived patient cell line (MDSL) into immunodeficient mice (NSG-SGM3) showed a 50-70% reduced graft upon UBE2N knockdown relative to a non-silencing control. The cellular effects of UBE2N inhibition correspond with suppression of TRAF6-induced NF-kappa beta activation of target genes. In addition, applicant found that NSC697923 treatment results in a dramatic loss of TRAF6 protein expression, which is rescued by inhibition of the proteasome. Intriguingly, the molecular analysis revealed that UBE2N inhibition shifts the stoichiometry of TRAF6 ubiquitin chains from K63-lined to K48-linked ubiquitin, resulting in proteasome-mediated degradation.

To identify the molecular basis of UBE2N inhibition, Applicant performed a global ubiquitin screen for changes in ubiquitinated substrates and gene expression profiling by RNA sequencing. For the ubiquitin screen, K63 ubiquinated proteins were immunopreciptated from MDSL cells upon pharmacologic inhibition of UBE2N, followed by mass spectrometry analysis. UBE2N inhibition significantly altered the ubiquitination of about 200 proteins involved in innate immune signaling, glycolysis, cell survival, RNA splicing, and DNA damage response. In parallel, RNA sequencing of MDSL cells treated with NSC697923 revealed expression changes in genes involved in mRNA processing, cell cycle, and glycolysis. Several components of the E3 ligase anaphase-promoting complex APC/CDC20 were downregulated after UBE2N inhibition. As expected, increased expression of APC/CDC20 substrates (i.e., cyclin B1) were 9 observed following treatment with NSC697923, suggesting that UBE2N inhibition in MDS/AML blocks degradation of APC/CDC20 targets and leads to mitotic alteration sand apoptosis.

One substrate identified in NSC697923-treated MDSL cells by the ubiquitin screen is DDB1, a component of the CUL4-CRBN E3 ligase complex targeted by Lenalidomide (LEN). Lenalidomide has been shown to be effective for treatment of myelodysplastic syndromes (MDS) and has significantly improved overall survival in myeloma (which formerly carried a poor prognosis), although toxicity remains an issue for users. LEN has shown encouraging results in del(5q) MDS patients ("deletion 5q (del 5q) MDS" in which part of chromosome 5 is missing), but its effects are limited in other cytogenetic subtypes of MDS or AML. Therefore, the identification of molecular targets that can enhance or extend the use of LEN in a broader spectrum of patients is desired Applicant explored the possibility of a cooperative effect of LEN and NSC697923 on MDS/AML cells. As compared to individual treatments, the combination of LEN and NSC697923 or UBE2N shRNAs significantly suppressed the function and viability of MDS/AML cell lines and patient samples in vitro. More striking, treatment of LEN and NSC697923 impaired MDS/AML cells that are refractory to treatment of LEN or NSC697923 alone. As such, UBE2N is a promising target for extending the use of LEN to other subtypes of MDS/AML.

Net, Applicant has identified a novel therapeutic target, an E2 ubiquitin conjugating enzyme (UBE2N) in MDS/AML. UBE2N inhibition suppresses the function and viability of MDS/AML cell lines and patient samples, due in part to degradation of TRAF6, suppressing innate immune signaling, and inducing mitotic alterations. Applicant has also found that inhibition of UBE2N alters ubiquitination of DDB1, a component of the CRBN complex, and cooperates with LEN to target MDS/AML cells.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating a myelodysplastic syndrome (MDS) and/or an acute myeloid leukemia (AML) comprising the step of administering one or more compounds selected from:

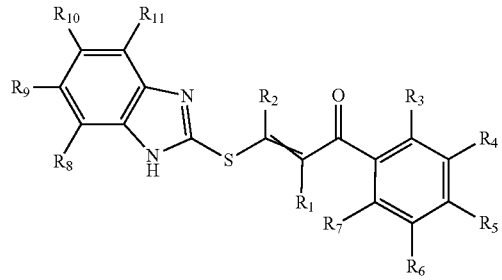

wherein $R_1$ is selected from H, F, Cl, Br, nitrile, $CH_3$, and $CH_2CH_3$;

$R_2$ is selected from H, F, Cl, and $C_1$-$C_4$ alkyl;

$R_3$, $R_4$, $R_6$, and $R_7$ are independently selected from H, F, Cl, Br, nitrile, $NHCOCH_3$, $C_1$-$C_4$ alkyl, $C_1$-$C_4$ alkoxy; and $R_4$ with either $R_3$ or $R_5$ are a substituted or unsubstituted benzo fused ring;

$R_5$ and $R_9$ are independently selected from H, F, Cl, Br, nitrile $NHCOCH_3$, methyl, ethyl, methoxy and ethoxy; and $R_8$ and $R_{10}$ are independently selected from H, F, Cl, Br, nitrile $NHCOCH_3$, $C_1$-$C_4$ alkyl, $C_1$-$C_4$ alkoxy.

2. The method of claim 1, wherein $R_1$, $R_2$, $R_3$, $R_4$, $R_6$, $R_7$, $R_8$, $R_{10}$, and $R_{11}$ are H.

3. The method claim 1, wherein the compound has the structure:

---

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Modified UBE2N Peptide
<220> FEATURE:
<221> NAME/KEY: Cysteine Carbamidomethylation (Cysteine CAM)
<222> LOCATION: (1)..(1)
<223> OTHER INFORMATION: N at position 1 is a Cysteine
      Carbamidomethylation (Cysteine CAM)
<220> FEATURE:
<221> NAME/KEY: Ubiquinated Lysine
<222> LOCATION: (6)..(6)
<223> OTHER INFORMATION: N at position 6 is ubiquinated lysine

<400> SEQUENCE: 1

Xaa Leu Asp Ile Leu Xaa Asp Lys Trp Ser Pro Ala Leu Gln Ile Arg
1               5                   10                  15
```

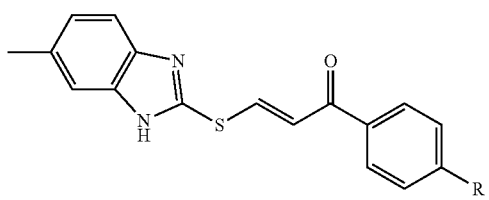

wherein R is selected from ethyl and methoxy.

4. The method of claim 1, wherein the compound is selected from

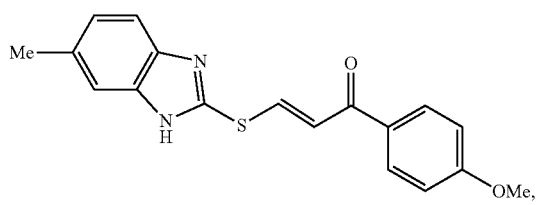
("UC65")

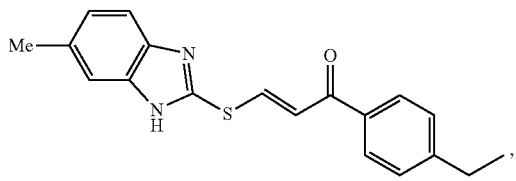
("UC64")

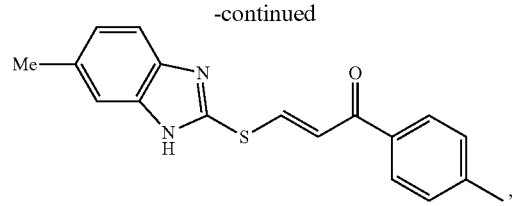

and combinations thereof.

5. The method of claim 1 wherein said one or more compounds is administered in an amount sufficient to activate one or both of TRAF6 and NF kappa beta.

6. The method of claim 1, wherein said one or more compounds is administered in an amount sufficient to slow or prevent growth of one or both of AML, and MDS cells, reduce clonogenic potential of one or both of AML and MDS cells, reduce viability of one or both of AML and MDS cells, promote apoptosis of one or both of AML and MDS cells, or combinations thereof.

7. The method of claim 1, wherein said one or more compounds is co-administered with lenalidomide ("LEN"), wherein said administration is in an amount sufficient to inhibit MDS/AML cell function.

8. The method of claim 1, wherein said one or more compounds is co-administered with a chemotherapeutic agent selected from a taxane, a platinum-based agent, an anthracycline, an alkylating agent, a *vinca* alkaloid, an epothilone, a histone deacetylase inhibitor, a topoisomerase I and II inhibitor, a kinase inhibitor, a nucleotide analog, a precursor analog, a peptide antibiotic, and combinations thereof.

9. A method of treating a non-del(5q) MDS patient, comprising the step of administering a compound or composition according to claim 1.

* * * * *